(12) United States Patent
Lorca

(10) Patent No.: US 9,987,313 B2
(45) Date of Patent: *Jun. 5, 2018

(54) *LACTOBACILLUS* SUPPLEMENT FOR ALLEVIATING TYPE 1 DIABETES

(71) Applicant: University of Florida Research Foundation, Incorporated, Gainesville, FL (US)

(72) Inventor: Graciela Liliana Lorca, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 308 days.

This patent is subject to a terminal disclaimer.

(21) Appl. No.: 14/656,209

(22) Filed: Mar. 12, 2015

(65) Prior Publication Data
US 2015/0182567 A1 Jul. 2, 2015

Related U.S. Application Data

(63) Continuation of application No. 13/144,028, filed as application No. PCT/US2010/024575 on Feb. 18, 2010, now Pat. No. 9,474,773.
(Continued)

(51) Int. Cl.
*A61K 35/74* (2015.01)
*A61K 35/747* (2015.01)
(Continued)

(52) U.S. Cl.
CPC .......... *A61K 35/747* (2013.01); *A23C 9/1234* (2013.01); *A23C 19/0323* (2013.01);
(Continued)

(58) Field of Classification Search
None
See application file for complete search history.

(56) References Cited

U.S. PATENT DOCUMENTS 5,556,785 A 9/1996 Kishida
6,214,336 B1 4/2001 Bukowska et al.
(Continued)

FOREIGN PATENT DOCUMENTS

| JP | 4044975 B | 2/1997 |
|---|---|---|
| WO | WO 2004/076615 A2 | 9/2004 |
| WO | WO 2008/141989 | 11/2008 |

OTHER PUBLICATIONS

Kin Kwan Lai, Graciela L. Lorca, and Claudio F. Gonzalez, Biochemical Properties of Two Cinnamoyl Esterases Purified from a Lactobacillus johnsonii Strain Isolated from Stool Samples of Diabetes-Resistant Rats, 2009, Applied and Environmental Microbiology, vol. 75, No. 15, p. 5018-5024.*
(Continued)

*Primary Examiner* — Renee Claytor
*Assistant Examiner* — Trent R Clarke
(74) *Attorney, Agent, or Firm* — Timothy H. Van Dyke; Beusse, Wolter, Sanks & Maire PLLC

(57) ABSTRACT

Isolated *Lactobacillus* strains are useful in preventing or delaying the development of Type 1 Diabetes (T1D). A probiotic composition comprising the *Lactobacillus* strains and use of the composition in T1D prevention are provided.

4 Claims, 12 Drawing Sheets

Related U.S. Application Data

(60) Provisional application No. 61/153,516, filed on Feb. 18, 2009, provisional application No. 61/297,480, filed on Jan. 22, 2010.

(51) Int. Cl.
    *A23C 9/123*     (2006.01)
    *A23C 19/032*     (2006.01)
    *A23G 9/36*     (2006.01)
    *C12N 1/20*     (2006.01)
    *A23L 33/135*     (2016.01)
    *A61K 35/00*     (2006.01)

(52) U.S. Cl.
    CPC ............ *A23G 9/363* (2013.01); *A23L 33/135* (2016.08); *C12N 1/20* (2013.01); *A23V 2002/00* (2013.01); *A23Y 2220/43* (2013.01); *A23Y 2220/71* (2013.01); *A61K 2035/115* (2013.01)

(56) References Cited

U.S. PATENT DOCUMENTS

| | | |
|---|---|---|
| 6,808,703 B2 | 10/2004 | Park et al. |
| 7,001,756 B1 | 2/2006 | Hsu et al. |
| 7,189,390 B2 | 3/2007 | Zink et al. |
| 7,390,519 B2 | 6/2008 | Collins et al. |
| 2003/0235559 A1 | 12/2003 | Sobol et al. |
| 2005/0100531 A1 | 5/2005 | Bienenstock |
| 2006/0270020 A1 | 11/2006 | Boileau et al. |
| 2008/0193485 A1 | 8/2008 | Gorbach et al. |

OTHER PUBLICATIONS

Kenneth Lau, Patrick Benitez, Alexandria Ardissone, Tenisha Wilson, Erin Collins, Graciela Lorca, Nan Li, Dhyana Sankar, Clive Wasserfall, Josef Neu, Mark Atkinson, Desmond Shatz, Eric Triplett, and Joseph Larkin, Inhibition of Type 1 Diabetes Correlated to a Lactobacillus johnsonii N6.2-Mediated Th17 Bias, 2011, J Immunol, vol. 186, pp. 3538-3546.*

Brugman, S. et al., "Antibiotic treatment partially protects against type 1 diabetes in the Bio-Breeding diabetes-prone rat. Is the gut flora involved in the development of type 1 diabetes?", *Diabetologia*, 2006, 49:2105-2108.

Calcinaro, F. et al., "Oral probiotic administration induces interleukin-10 production and prevents spontaneous autoimmune diabetes in the non-obese diabetic mouse," *Diabetologia*, 2005, 48:1565-1575.

Like, A.A. et al., "Influence of environmental viral agents on frequency and tempo of diabetes mellitus in BB/Wor rats," *Diabetes*, 1991, 40(2): 259-262, abstract.

Matsuzaki, Takeshi et al., "Prevention of onset in an insulin-dependent diabetes mellitus model, NOD mice, by oral feeding of *Lactobacillus casei*," *Acta Pathologica, Microbiologica et Immunologica Scandinavica (APMIS)*, 1997, 105:643-649.

McInerney, M.F. et al., "Prevention of insulitis and diabetes onset by treatment with complete Freund's adjuvant in NOD mice," *Diabetes*, 1991, 40(6):715-725, abstract.

Sadelain, M.W. et al., "Prevention of type I diabetes in NOD mice by adjuvant immunotherapy," *Diabetes*, 1990, 39(5):583-589, abstract.

Sadelain, Michael W. J. et al., "Prevention of Diabetes in the BB Rat by Early Immunotherapy Using Freund's Adjuvant," *Journal of Autoimmunity*, 1990, 3:671-680.

Salminen, Seppo et al., "Intestinal colonistation, microbiota and future probiotics?," *Asia Pacific Journal of Clinical Nutrition*, 2006, 15(4):558-562.

Satoh, Jo et al., "Treatment With Streptococcal Preparation (OK-432) Suppresses Anti-Islet Autoimmunity and Prevents Diabetes in BB Rats," *Diabetes*, Sep. 1988, 37:1188-1194.

Schwartz, R.F. et al., "Comment on: Brugman S. et al. (2006) Antibiotic treatment partially protects against type 1 diabetes in the Bio-Breeding diabetes-prone rat. Is the gut flora involved in the development of type 1 diabetes? Diabetologia, 49:.2105-2108," *Diabetologia*, 2007, 50:220-221.

Shori, Amal B., "Antioxidant activity and viability of lactic acid bacteria in soybean-yogurt made from cow and camel milk," *Journal of Taibah University for Science*, 2013, 7:202-208.

Vaarala, Outi et al., "The "Perfect Storm" for Type 1 Diabetes: The Complex Interplay Between Intestinal Microbiota, Gut Permeability, and Mucosal Immunity," 2008, *Diabetes*, 57(10):2555-2562.

Wicker, Linda S. et al., "Genetic Control of Diabetes and Insulitis in the Nonobese Diabetic (NOD) Mouse," *The Journal of Experimental Medicine*, 1987, 165:1639-1654.

Yadav, Hariom et al., "Antidiabetic effect of probiotic dahi containing *Lactobacillus acidophilus* and *Lactobacillus casei* in high fructose fed rats," *Nutrition*, 2007, 23:62-68.

Yamano, Toshihiko et al., "Effects of the probiotic strain *Lactobacillus johnsonii* strain La1 on autonomic nerves and blood glucose in rats," *Life Sciences*, 2006, 79:1963-1967.

\* cited by examiner

FIG. 2A-1 PCA - Qualitative - A
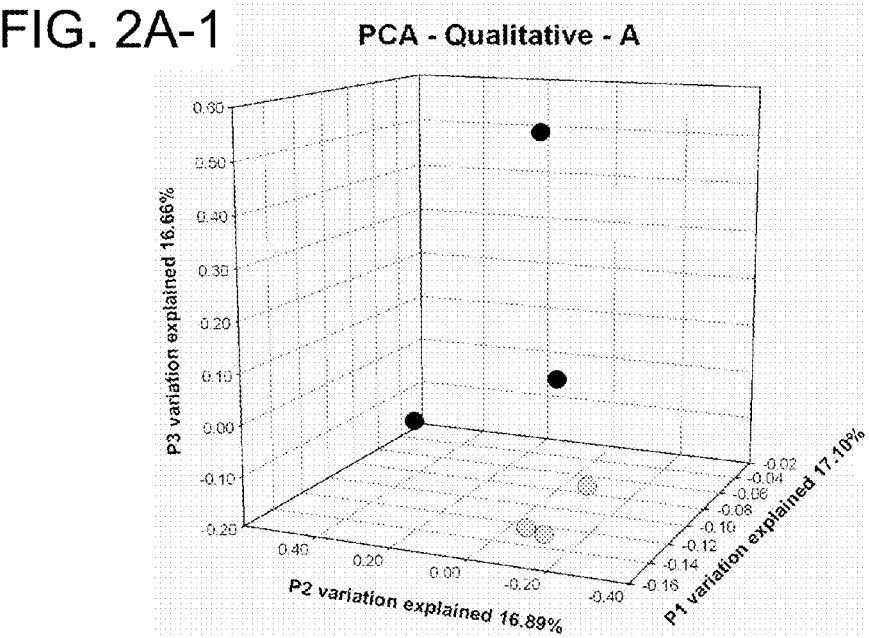
FIG. 2A-2 PCA - Quantitative - A
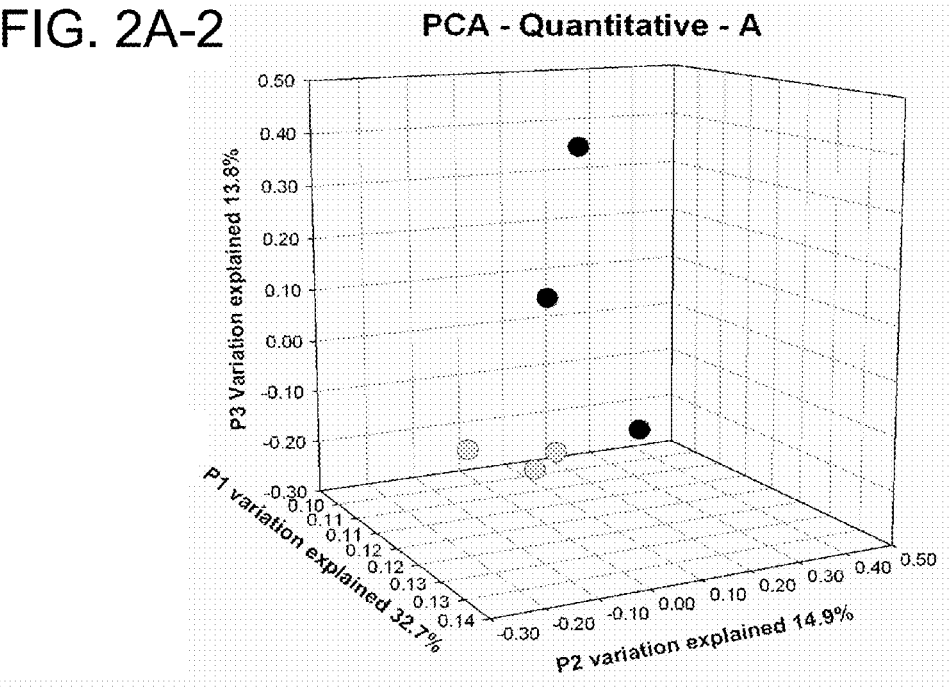
○ BioBreeding Diabetes prone
● BioBreeding Diabetes resistant

- BioBreeding Diabetes prone
- BioBreeding Diabetes resistant

LACTOBACILLUS SUPPLEMENT FOR ALLEVIATING TYPE 1 DIABETES

CROSS-REFERENCE TO A RELATED APPLICATION

This application is a continuation application of U.S. application Ser. No. 13/144,028, filed Oct. 4, 2011, which is a national phase application of International Application No. PCT/US2010/024575, filed Feb. 18, 2010, which claims the benefit of U.S. provisional application Ser. No. 61/153,516, filed Feb. 18, 2009 and U.S. provisional application Ser. No. 61/297,480, filed Jan. 22, 2010, all of which are incorporated herein by reference in their entirety.

The Sequence Listing for this application is labeled "April2012-ST25.txt", which was created on Apr. 2, 2012, and is 16 KB. The entire content is incorporated herein by reference in its entirety.

BACKGROUND OF INVENTION

Diabetes mellitus is a family of disorders characterized by chronic hyperglycemia and the development of long-term vascular complications. This family of disorders includes type 1 diabetes, type 2 diabetes, gestational diabetes, and other types of diabetes.

Immune-mediated (type 1) diabetes (or insulin dependent diabetes mellitus, IDDM) is a disease of children and adults for which there currently is no adequate means for prevention or cure. Type 1 diabetes, represents approximately 10% of all human diabetes. The disease is characterized by an initial leukocyte infiltration into the pancreas that eventually leads to inflammatory lesions within islets, a process called "insulitis".

Type 1 diabetes is distinct from non-insulin dependent diabetes (NIDDM) in that only the type 1 form involves specific destruction of the insulin producing beta cells of the islets of Langerhans. The destruction of beta cells appears to be a result of specific autoimmune attack, in which the patient's own immune system recognizes and destroys the beta cells, but not the surrounding alpha cells (glucagon producing) or delta cells (somatostatin producing) that comprise the pancreatic islet. The progressive loss of pancreatic beta cells results in insufficient insulin production and, thus, impaired glucose metabolism with attendant complications.

The factors responsible for type 1 diabetes are complex and thought to involve a combination of genetic, environmental, and immunologic influences that contribute to the inability to provide adequate insulin secretion to regulate glycemia.

The natural history of type 1 diabetes prior to clinical presentation has been extensively studied in search of clues to the etiology and pathogenesis of beta cell destruction. The prediabetic period may span only a few months (e.g., in very young children) to years (e.g., older children and adults). The earliest evidence of beta cell autoimmunity is the appearance of various islet autoantibodies. Metabolically, the first signs of abnormality can be observed through intravenous glucose tolerance testing (IVGTT). Later in the natural history of the disease, the oral glucose tolerance test (OGTT) typically becomes abnormal. With continued beta cell destruction and frank insulinopenia, type 1 diabetes becomes manifest.

Type 1 diabetes occurs predominantly in genetically predisposed persons. Concordance for type 1 diabetes in identical twins is 30-50% with an even higher rate of concordance for beta cell autoimmunity, as evidenced by the presence of islet autoantibodies in these individuals (Pyke, D. A., 1979. "Diabetes: the genetic connections." *Diabetologia* 17: 333-343). While these data support a major genetic component in the etiopathogenesis of type 1 diabetes, environmental or non-germline genetic factors must also play important pathologic roles. Environmental factors proposed to date include viral infections, diet (e.g., nitrosamines in smoked meat, infant cereal exposure), childhood vaccines, lack of breast-feeding, early exposure to cows' milk, and aberrant intestinal functioning (Vaarala et al. 2008). Hence, while the list of potential environmental agents for type 1 diabetes is large, the specific environmental trigger(s) that precipitate beta cell autoimmunity remain elusive.

Type 1 diabetes is currently managed by the administration of exogenous human recombinant insulin. Although insulin administration is effective in achieving some level of euglycemia in most patients, it does not prevent the long-term complications of the disease including ketosis and damage to small blood vessels, which may affect eyesight, kidney function, blood pressure and can cause circulatory system complications.

Although knowledge of the immune system has become much more extensive in recent years, the precise etiology of type 1 diabetes remains a mystery. Furthermore, despite the enormously deleterious health and economic consequences, and the extensive research effort, there currently is no effective means for controlling the formation of this disease.

As noted above, one of the numerous factors that has been considered in the context of unraveling the complex etiology of type 1 diabetes is intestinal functioning, including the interaction of intestinal microflora. The presence of a commensal intestinal microbiota in infancy is critical and well documented for numerous physiologic processes including growth, angiogenesis, optimization of nutrition, and stimulation of various arms of the innate and adaptive immune systems. However, similar studies in T1D are limited. In rodent models of T1D, the disease is likely to develop under germ free conditions. Diabetes prone rats (BB-DP) subjected to cesarean derivation develop accelerated disease (Like et al. 1991). In terms of using such information to proactively modulate diabetes formation, the antibiotic treatments to BB-DP rats after weaning (Brugman et al. 2006) prevents diabetes, whereas with the NOD mouse, a decreased frequency of T1D was observed with the administration of doxycycline (Schwartz et al. 2007). Probiotic treatment of non-obese diabetic mice (NOD) prevents the onset of T1D (Calcinaro et al. 2005; Yadav et al. 2007). Similarly, a low fat diet with *Lactobacillus* strains reduced insulin-dependent diabetes in rats (Matsuzuki et al. 2007). Antibiotics can prevent T1D in diabetes-prone rats (BB-DP) (Brugman et al. 2006) and in NOD mice (Schwartz et al. 2006). The incidence of diabetes in NOD mice increases in a germ-free environment (Suzuki et al. 1987; Wicker et al. 1987). Freund's adjuvant, which contains mycobacteria, also protects NOD mice and the BB-DP rat against diabetes (Sadelain et al. 1990a,b; McInerney et al. 1991). The specific mechanisms of how such therapies modulate disease are unclear.

BRIEF SUMMARY

The subject invention provides compositions for alleviating type 1 diabetes (T1D). In preferred embodiments, the compositions comprise an effective amount of one or more *Lactobacillus* isolates. Preferably, the bacteria used as an active ingredient in the compositions of the subject invention are a *Lactobacillus reuteri* strain, a *Lactobacillus johnsonii* strain, or a combination thereof.

The subject invention also provides methods for preventing or slowing the development of T1D. These methods comprise the administration of a composition of the subject invention, wherein the composition preferably comprises an effective amount of one or more *Lactobacillus* isolates.

BRIEF DESCRIPTION OF THE SEQUENCES

SEQ ID NO: 1 is a primer useful according to the subject invention.
SEQ ID NO: 2 is a primer useful according to the subject invention.
SEQ ID NO: 3 is a primer useful according to the subject invention.
SEQ ID NO: 4 is a primer useful according to the subject invention.
SEQ ID NO: 5 is a primer useful according to the subject invention.
SEQ ID NO: 6 is a primer useful according to the subject invention.
SEQ ID NO: 7 is a primer useful according to the subject invention.
SEQ ID NO: 8 is a primer useful according to the subject invention.
SEQ ID NO: 9 is a primer useful according to the subject invention.
SEQ ID NO: 10 is a primer useful according to the subject invention.
SEQ ID NO: 11 is a primer useful according to the subject invention.
SEQ ID NO: 12 is a primer useful according to the subject invention.
SEQ ID NO: 13 is a primer useful according to the subject invention.
SEQ ID NO: 14 is a primer useful according to the subject invention.
SEQ ID NO: 15 is a primer useful according to the subject invention.
SEQ ID NO: 16 is a primer useful according to the subject invention.
SEQ ID NO: 17 is a primer useful according to the subject invention.
SEQ ID NO: 18 is a primer useful according to the subject invention.
SEQ ID NO: 19 is a primer useful according to the subject invention.
SEQ ID NO: 20 is a primer useful according to the subject invention.
SEQ ID NO: 21 is a primer useful according to the subject invention.
SEQ ID NO: 22 is a primer useful according to the subject invention.
SEQ ID NO: 23 is a primer useful according to the subject invention.
SEQ ID NO: 24 is a primer useful according to the subject invention.
SEQ ID NO: 25 is a primer useful according to the subject invention.
SEQ ID NO: 26 is a primer useful according to the subject invention.
SEQ ID NO: 27 is a primer useful according to the subject invention.
SEQ ID NO: 28 is a primer useful according to the subject invention.
SEQ ID NO: 29 is a primer useful according to the subject invention.
SEQ ID NO: 30 is a primer useful according to the subject invention.
SEQ ID NO: 31 is a primer useful according to the subject invention.
SEQ ID NO: 32 is a primer useful according to the subject invention.
SEQ ID NO: 33 is a primer useful according to the subject invention.
SEQ ID NO: 34 is a primer useful according to the subject invention.
SEQ ID NO: 35 is a primer useful according to the subject invention.
SEQ ID NO: 36 is a primer useful according to the subject invention.
SEQ ID NO: 37 is a primer useful according to the subject invention.
SEQ ID NO: 38 is a primer useful according to the subject invention.
SEQ ID NO: 39 is a primer useful according to the subject invention.
SEQ ID NO: 40 is a primer useful according to the subject invention.
SEQ ID NO: 41 is a primer useful according to the subject invention.
SEQ ID NO: 42 is a primer useful according to the subject invention.
SEQ ID NO: 43 is a primer useful according to the subject invention.
SEQ ID NO: 44 is a primer useful according to the subject invention.
SEQ ID NO: 45 is a primer useful according to the subject invention.
SEQ ID NO: 46 is a primer useful according to the subject invention.
SEQ ID NO: 47 is a primer useful according to the subject invention.
SEQ ID NO: 48 is a primer useful according to the subject invention.
SEQ ID NO: 49 is a primer useful according to the subject invention.
SEQ ID NO: 50 is a primer useful according to the subject invention.
SEQ ID NO: 51 is a primer useful according to the subject invention.
SEQ ID NO: 52 is a primer useful according to the subject invention.
SEQ ID NO: 53 is a primer useful according to the subject invention.
SEQ ID NO: 54 is a primer useful according to the subject invention.
SEQ ID NO: 55 is a primer useful according to the subject invention.
SEQ ID NO: 56 is a primer useful according to the subject invention.
SEQ ID NO: 57 is a primer useful according to the subject invention.
SEQ ID NO: 58 is a primer useful according to the subject invention.
SEQ ID NO: 59 is a primer useful according to the subject invention.
SEQ ID NO: 60 is a primer useful according to the subject invention.
SEQ ID NO: 61 is a primer useful according to the subject invention.

SEQ ID NO: 62 is a primer useful according to the subject invention.

SEQ ID NO: 63 is a primer useful according to the subject invention.

SEQ ID NO: 64 is a primer useful according to the subject invention.

SEQ ID NO: 65 is a primer useful according to the subject invention.

SEQ ID NO: 66 is a primer useful according to the subject invention.

SEQ ID NO: 67 is a primer useful according to the subject invention.

SEQ ID NO: 68 is a primer useful according to the subject invention.

SEQ ID NO: 69 is a primer useful according to the subject invention.

SEQ ID NO: 70 is a primer useful according to the subject invention.

SEQ ID NO: 71 is a primer useful according to the subject invention.

BRIEF DESCRIPTION OF DRAWINGS

FIGS. 2A1-2A2 and 2B1-2B2 show the principal coordinates analysis (PCA) depicting the qualitative (presence/absence) and quantitative (presence/absence and abundance) of the bacterial communities for the 10 stool samples each from the diabetes-resistant and diabetes-prone rats. This analysis is based on the community structures derived from experiment 1's Sanger sequencing (2A1-A2) and experiment 2's pyrosequencing (2B1-B2).

DETAILED DISCLOSURE

Figure 1:
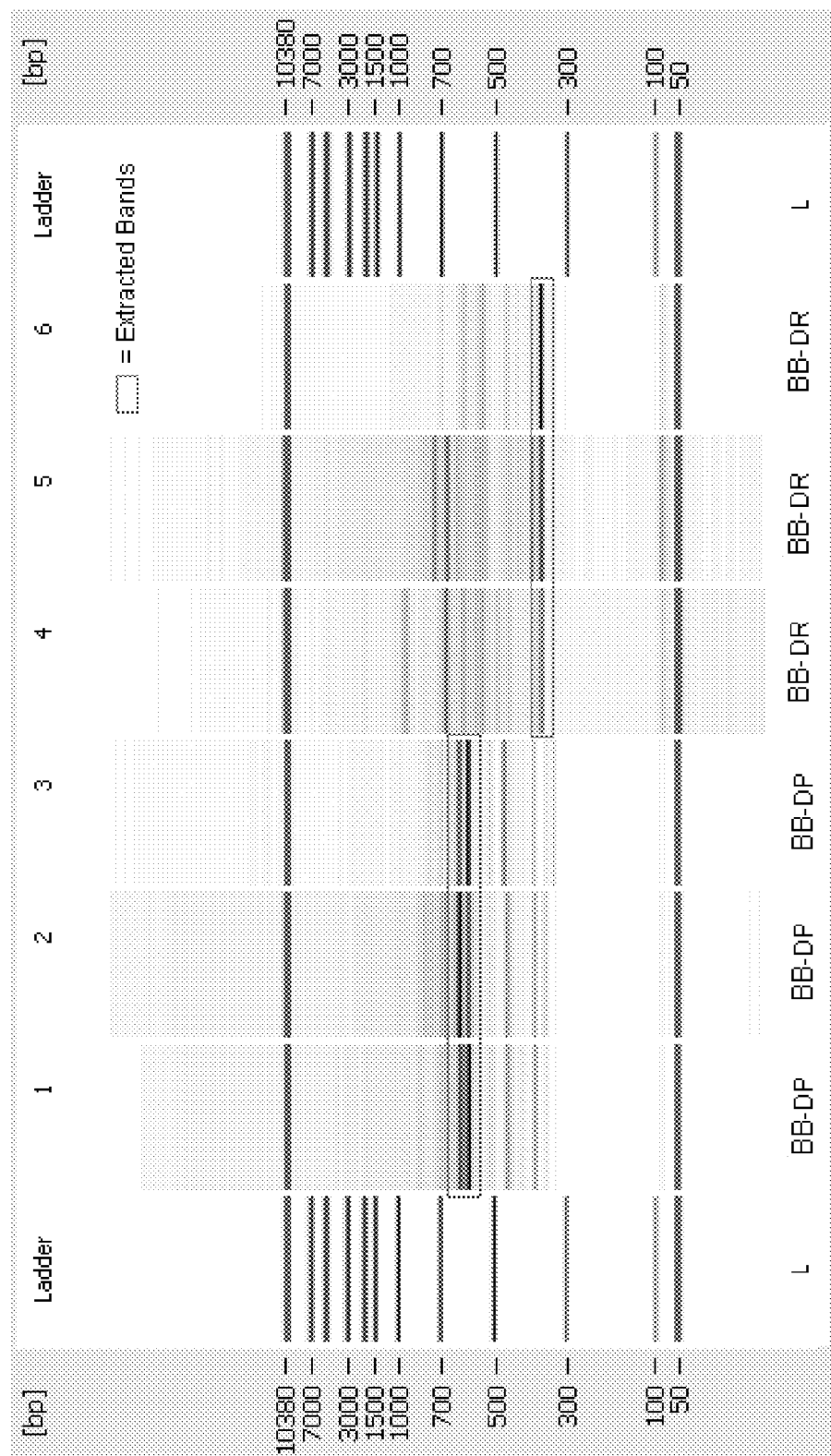
FIG. 1 shows a gel-like image generated by a bioanalyzer. The first and last columns are the reference DNA 7500 ladder. Base pair sizes are indicated adjacent to the ladder. Samples 1 to 3 represent the ARISA profiles for the intestinal tract of diabetes prone (BB-DP) and samples 4 to 6 represent diabetes resistant (BB-DR) rats' stool samples at 60 days of age. The lower most (50 bp) and the upper most (10380 bp) bands represent the markers used to align the ladder data with data from the sample wells. The boxes represent dominant bands unique to both group and were extracted from the gel for further sequencing. The stool samples used in the ARISA analysis come from experiment 1.

In accordance with the subject invention, it has been found that *Lactobacillus* strains can be used to alleviate (delay the onset of, and/or reduce the severity or progression of), type 1 diabetes (T1D). In specific embodiments of the subject invention, the administration of *Lactobacillus* strains such as *L. johnsonii* can prevent or delay the onset of, or reduce the progression of, T1D.

In one embodiment, the subject invention provides isolated *Lactobacillus* strains that are able to delay and/or prevent the development of T1D. The preferred strains include *Lactobacillus reuteri* and *Lactobacillus johnsonii*. In one embodiment the bacteria is *L. johnsonii*. Specially exemplified herein is *Lactobacillus johnsoni* N6.2.

A culture of *Lactobacillus johnsoni* N6.2 has been deposited with the American Type Culture Collection (ATCC), 10801 University Blvd., Manassas, Va. 20110-2209 USA. The deposit has been assigned accession number ATCC No. PTA-122064 by the repository and was deposited on Mar. 19, 2015.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

In accordance with the subject invention, it has been found that the oral transfer of *Lactobacillus johnsonii* N6.2 from DR rodents to DP rodents conferred T1D resistance to DP rodents. Diabetes resistance in *Lactobacillus johnsonii* N6.2 fed DP rodents was correlated to a TH17 bias within the mesenteric lymph nodes which was associated with high levels of IL6 and IL23. Moreover, in vitro assays showed that *Lactobacillus johnsonii* N6.2 mediated high IL6 levels in antigen presenting cells which can mediate TH17 differentiation in the presence of sufficient TCR stimulation.

A thorough, culture-independent examination of the diversity of bacteria in the stool of diabetes-prone (DP) and diabetes-resistant (DR) rats just prior to the onset of diabetes was done by a variety of culture-independent approaches. The results of all approaches were in agreement that certain bacterial species are more common in diabetes-resistant than in diabetes-prone rats. The results were verified with two genera using quantitative PCR.

In these 16S rRNA libraries, close relatives of 74 genera were identified. Of those, 18 genera showed higher abundance in one rat genotype versus the other. Of the 9 genera with higher abundance in BB-DR, three genera, *Bifidobacterium*, *Lactobacillus*, and *Pseudobutyrivibrio*, have representatives with known probiotic activity. These observations from pyrosequencing were verified by qPCR of *Bifidobacterium* and *Lactobacillus*. These results also confirmed the BB-DR specific ARISA band identified in Example 1 as *Lactobacillus*. These bacteria may prevent the growth of other strains that cause a leaky gut epithelium and/or cause an altered immune response against gut microbiota.

Of the 9 genera in higher abundance in BB-DP, none are known to have probiotic activity. As expected in stool samples, there are many genera that are strict anaerobes and these genera are found in BB-DR and BB-DP samples. A halophilic genus, *Pontibacillus*, is found in much higher numbers in BB-DP samples. These observations are consistent with previous work where feeding probiotics or antibiotics to either NOD mice or BB-DP rats prevented diabetes (Brugman et al. 2006; Calcinaro et al. 2005; Matsuzuki et al. 2007; Yadav et al. 2007).

However, species-level differences reveal changes not seen at the genus level. Perhaps the most dramatic example of this is *Clostridium*. At the genus level, *Clostridium* abundance does not differ between BB-DR and BB-DP. However, five species of *Clostridium* are higher in BB-DP than in BB-DR. Only one *Clostridium* species, *C. hylemonae*, is higher in BB-DR than in BB-DP. However, of the six species, *C. hylemonae* appears to be by far the least abundant of these six species. Twenty-one other species of *Clostridium* were identified in these samples but they did not differ between the two genotypes (Table 1).

Several exogenous as well as endogenous factors could affect the intestinal microbiota in these rats. The environment of these animals including food intake was the same in both BB-DP and BB-DR rats, thus minimizing its contributions to the differences in intestinal microbiota observed between the two strains. Factors other than the environment and genetic background have been shown to contribute to gut microbiota composition.

However, in the work that led to the subject invention, these external factors have been minimized. All rats were provided the same lighting, temperature, diet, water, and cage conditions. BB-DR and BB-DP were in separate cages with two or three rats per cage after weaning from the mother.

A striking feature of this work is the large number of Operational Taxonomy Units (OTUs) that differed between BB-DP and BB-DR but could not be classified to a known genus. At the family level, there were striking taxonomic trends with the Clostridiaceae and Ruminococcaceae more prevalent in BB-DP while the Lachnospiraceae, Porphyromonadaceae, and Prevotellaceae were more common in BB-DR. This suggests a selectivity in the changes that occur in the BB-DP gut over time. Certain taxa appear to be targeted for loss over time in BB-DP. These may be under attack from the immune system or the conditions in the BB-DP gut may be less conducive to their growth.

One embodiment of the subject invention provides a probiotic composition for preventing and/or delaying the onset of T1D (or reducing the severity of T1D) comprising an effective amount of one or more *Lactobacillus* isolates. The composition can also include pharmaceutically acceptable carriers, additives, or excipients. In one embodiment, the composition includes one or more other probiotic materials.

The amount of the therapeutic or pharmaceutical composition of the invention that is effective in the prevention and/or treatment of T1D can be determined by a person skilled in the art having the benefit of the current disclosure through standard clinical techniques. Relevant factors include, but are not limited to, the type(s) of *Lactobacillus* strain, the particular physiological symptom or condition, the severity of the disease or condition including the presence or absence of the translocation of normal flora and/or its metabolites, and the degree of the translocation of normal flora and/or its metabolites. The precise dose to be employed in the formulation will also depend on the route of administration, and should be decided according to the judgment of the practitioner and each patient's circumstances. In one embodiment, effective doses can be extrapolated from dose-response curves derived from in vitro or animal model test systems.

In certain embodiments, the subject composition is administered to a subject at a dosage ranging from $10^2$ to $10^{11}$ *Lactobacillus* per day. In a specific embodiment, the subject composition comprises about $10^2$ to $10^5$ *L. reuteri* as an active ingredient. In another specific embodiment, the subject composition comprises about $10^2$ to $10^5$ *L. johnsonii* as an active ingredient.

The *Lactobacillus* strains of the subject invention can be formulated according to known methods for preparing pharmaceutically useful compositions. Formulations are described in a number of sources, which are well known and readily available to those skilled in the art. For example, *Remington's Pharmaceutical Science* (Martin E W [1995] Easton Pa., Mack Publishing Company, 19$^{th}$ ed.) describes formulations that can be used in connection with the subject invention. It should be understood that in addition to the ingredients particularly mentioned above, the formulations of the subject invention can include other agents conventional in the art having regard to the type of formulations described herein.

In addition, *Lactobacillus* can be administered simultaneously or sequentially with an antioxidant that provides defenses against cellular oxidative damage. Suitable antioxidants include, but are not limited to, vitamins, minerals, peptides, enzymes, coenzymes, and metabolites, which are involved in the reduction of the oxidative stress in a subject. In one embodiment, the antioxidant is vitamin E. The term "vitamin E," as used herein, includes, but is not limited to, eight different chemical forms: four tocopherols and four tocotrienols. In a specific embodiment, vitamin E is alpha-tocopherol. In certain embodiments, the antioxidant may be, for example, selenium, glutathione, vitamin C, vitamin E, carotenes (including beta carotene and retinol), or ubiquinone, or a combination thereof.

Strains of *Lactobacillus reuteri* are available from various public culture collections, including the American Type Culture Collection (ATCC, USA), ATCC 23272, 53608, 53609, 55148, and 55739; Deutsche Sammlung von Mikroorganismenn und Zellkulturen GmbH (DSMZ, Germany), DSM 8533, 17509, 20015, 20016, 20053, and 20056; Czechoslovak Collection of Microorganisms (CCM, Czech Republic), CCM 3625, 3642, 3643, 3644, and 3645; and National Collection of Industrial and Marine Bacteria (NCIMB, Scotland), NCIMB 11951, 701089, 701359, 702655, and 702656. Strains of *Lactobacillus johnsonii* are also available from various public culture collections, including the American Type Culture Collection (ATCC, USA), ATCC 332, 11506, and 33200; Deutsche Sammlung von Mikroorganismenn und Zellkulturen GmbH (DSMZ, Germany), DSM 10533 and 20553; Czechoslovak Collection of Microorganisms (CCM, Czech Republic), CCM 2935, and 4384; and National Collection of Industrial and Marine Bacteria (NCIMB, Scotland), NCIMB 8795, and 702241.

The *Lactobacillus* strain can be a mutant having substantially the same or improved properties or it can be a naturally-occurring variant thereof. Procedures for making mutants are well known in the microbiological art. Ultraviolet light and nitrosoguanidine are used extensively toward this end.

The composition of the subject invention can be administered in any suitable way, preferably orally. The pharmaceutically-acceptable carriers, additives, or excipients can be any suitable food products, such as milk, oats, wheat, corn, potatoes, green bananas, etc.

In one embodiment, the bacteria of the subject invention are administered in the form of a capsule (as dehydrated bacteria) as a food supplement. This will assure that the microorganisms survive through the gastrointestinal tract passage and exert their beneficial effect in the intestine.

Diet can be an important factor in the development of type 1 diabetes. For example, diets low in milk components or hydrolysed casein-based diets reduce the incidence of type 1 diabetes in BB-DP animals because protein components in milk have certain sequence identity to pancreatic antigens.

The subject invention further provides a method of preventing or slowing the development of T1D comprising administration of a composition comprising an effective amount of one or more *Lactobacillus* isolates together with diet modification.

Other autoimmune conditions to which the treatments of the subject invention may be applied include, but are not limited to, rheumatoid arthritis, multiple sclerosis, thyroiditis, inflammatory bowel disease, Addison's disease, pancreas transplantation, kidney transplantation, islet transplantation, heart transplantation, lung transplantation, and liver transplantation.

Therapeutic Benefits of *Lactobacillus*

The several mechanisms by which *Lactobacillus* can exert beneficial effects for the host include, but are not limited to, (i) as a physical barrier inhibiting the passage of inflammatory antigens, (ii) degradation of toxic components, (iii) release of nutrients and, (iv) production of anti-inflammatory compounds.

In addition, *Lactobacillus* strains may exert their beneficial effects through proteolytic activity by degradation of putative pro-diabetogenic components in the diet. Further, *Lactobacillus* strains, can hydrolyze the fiber components in the diet with the concomitant release of antioxidant compounds.

*Lactobacillus* Promotes Intestinal Barrier Function.

One beneficial effect of *Lactobacillus* is that it can promote intestinal barrier function, thereby inhibiting the passage of inflammatory antigens.

*Lactobacillus* can inhibit the growth of pathogenic bacteria. *Lactobacillus* can produce a direct inhibitory effect on enterobacteria, partially through host modifications in epithelial composition. The administration of *Lactobacillus* lowers Enterobacteriaceae counts in the cecum and colon. In stools the microbiota composition was not affected by the administration of *L. johnsonii* N6.2. However, a negative correlation between lactobacilli and enteric bacteria was found in the intestinal mucosa.

In addition, *Lactobacillus* is capable of preventing or reducing bacteria translocation in a subject. The early administration of *Lactobacillus* strains to BB-DP pups (2-7-day-old) decreased bacterial translocation to the spleen and liver, indicating that *Lactobacillus* produced a beneficial effect on the gastrointestinal epithelia.

Further, the administration of *Lactobacillus* can increase the level of goblet cells in a subject, thereby inhibiting enteric bacteria population. Goblet cells constantly produce mucus, which has a dual role of protecting the mucosa from adhesion of certain microorganisms to the epithelia while providing an initial binding site, nutrient source, and matrix on which bacteria can proliferate.

As exemplified herein, a higher number of goblet cells in the *L. johnsonii* fed and healthy control groups were observed compared to the diabetic group. The increase in goblet cells reflects higher mucus production.

Further, *L. plantarum* has a direct effect on epithelial cells by inducing secretion of mucins that diminish enteric pathogens binding to mucosal epithelial cells. Mucus production is a characteristic associated with animals that did not develop diabetes.

In addition, claudin-1 expression is induced following feeding of *L. johnsonii*, indicating a direct effect of the probiotic bacteria on intestinal barrier function.

*Lactobacillus* Facilitates the Release of Antioxidant Compounds.

A further beneficial effect of *Lactobacillus* is that it facilitates the release of antioxidant compounds by probiotic bacteria. The release of antioxidant compounds contributes to an enhanced oxidative stress response.

Adherence of *Lactobacillus*, such as for example, *L. johnsonii* to the intestinal epithelium, along with increased mucus secretion, decreases the passage of inflammatory compounds that irritate the mucosa and result in the generation of reactive oxygen species. *Lactobacillus* strains such as *L. johnsonii* are capable of targeting an early step in the signaling pathway, possibly Indoleamine 2,3-Dioxygenase (IDO), resulting in a more tolerogenic environment that reduces the overall oxidative stress environment conducive to a subsequent inflammatory response. As a result, *Lactobacillus* strains such as *L. johnsonii* can delay or prevent the onset of autoimmunity that leads to type 1 diabetes.

In addition, *Lactobacillus* species have cinnamic acid esterase activity, which makes them capable of alleviating oxidative stress and inflammation exhibited in diabetes. 80% of lactobacilli negatively correlated with the onset of diabetes in BB-DR rats have cinnamic acid esterase activity; while only 41% of the lactobacilli isolated from the BB-DP animals were positive.

Cinnamic acids are natural bioactive phenolic compounds extensively associated with anti-inflammatory and antioxidant properties. These acids (ferulic, di-ferulic, p-coumaric) are esterified in vegetable cell walls and consequently are assimilated by the intestinal tract only after microbiota-mediated enzymatic release. Small doses of ferulic acid decrease the incidence of diabetes in streptozotocin (STZ)-induced diabetic mice. Thus, phenolic compounds such as ferulic acid released by gut microbiota play a critical role in alleviating the oxidative stress and attenuating the hyperglycemic inflammatory response exhibited in diabetes.

Specifically, the *L. johnsonii* strain possesses two esterases that can release cinnamic and other phenolic compounds with anti-inflammatory properties. The release of cinnamic acids from dietary components can decrease diabetic incidents, as observed in the *L. johnsonii* N6.2 fed group in Example 11.

Advantageously, the administration of *Lactobacillus* according to the subject invention can produce an anti-oxidative effect in a subject. As described in Example 11, the oxidative status of the ileac mucosa was assessed by measuring the mRNA levels of genes involved in the oxidative stress response. The expression of enzymes involved in the detoxification of ROS will be induced if an oxidative environment is generated. The genes encoding Sod2, Gpx1, Cat, and GR were induced in diabetic animals; while their levels decreased in healthy animals. Gpx1 and Sod2 expression levels were even lower in the *L. johnsonii* N6.2 fed group, indicating a lower level of ROS.

In addition, the administration of *Lactobacillus* according to the subject invention can reduce the production of nitric oxide in a subject. Nitric oxide is a signaling molecule that links inflammation and the development of type 1 diabetes. An increased transcription and translation of the iNOS gene is associated with diabetes in BB-DP rats. The active participation of nitric oxide during the early stage of autoimmune diabetes was confirmed by specific inhibition of iNOS using aminoguanidine (AG). BB-DR rats treated with AG do not developed diabetes after Kilham rat virus (KRV) infection. As described in Examples 12-13, the expression level of iNOS (and its inducing cytokine, IFNγ) was down-regulated in the *L. johnsonii* N6.2 fed group, as compared to untreated diabetic rats.

The administration of *Lactobacillus* can also increase the levels of Cox-2 expression. Cox-2 has been reported to be mainly induced in activated macrophages and other inflammatory cells. The presence of Cox-2 and insulin in β-cells decreased during progression of diabetes in the non-obese diabetic (NOD) mouse model. The expression of Cox-2 (and their specific prostaglandins) has a general protective effect on a subject. In addition, the synthesis of cyclopentenone prostaglandins is determinant during inflammatory resolution.

As described in Example 11, the mRNA levels of Cox-2 in the small intestine were gradually increased in the healthy animals, with the highest expression in the *L. johnsonii* fed animals. The increase in Cox-2 expression correlates with a higher number of goblet cells in the intestine of healthy rats.

Timing of Treatment

The therapies of the subject invention can be used to alleviate type 1 diabetes.

In one embodiment, treatment is administered prior to the onset of clinical manifestation of overt type 1 diabetes. The time of administration is preferably before extensive irreversible beta cell destruction as evidenced by, for example, the clinical onset of type 1 diabetes.

As set forth in more detail below with respect to type 1 diabetes, those skilled in the art, having the benefit of the instant disclosure can utilize diagnostic assays to assess the stage of disease progression in a patient and then administer treatment at the appropriate time as set forth herein.

With regard to the early detection of type 1 diabetes, numerous autoantibodies have been detected that are present at the onset of type 1 diabetes. Also, new serologic markers associated with type 1 diabetes continue to be described. Four islet autoantibodies appear to be the most useful markers of type 1 diabetes: islet cell antibodies (ICA), insulin autoantibodies (IAA), glutamic acid decarboxylase autoantibodies (GADA), and insulinoma-associated-2 autoantibodies (IA-2A). These are discussed in more detail below; however, the use of these markers to identify those at risk for developing type 1 diabetes is well known to those skilled in the art. In a specific embodiment of the subject invention, treatment is administered when a patient has at least one antibody marker or, preferably, at least two of the antibody markers.

ICA serve an important role as serologic markers of beta-cell autoimmunity. Seventy percent or more of Caucasians are ICA-positive at onset of type 1 diabetes. Following diagnosis, ICA frequency decreases, and fewer than 10% of patients still express ICA after 10 years. The general population frequency of ICA is between 0.1% and 0.3%. In a preferred embodiment of the subject invention, ATG is administered prior to a decrease in ICA.

IAA occur in 35-60% of children at onset of type 1 diabetes but are less common in adults. For example, in Australians with new-onset type 1 diabetes, IAA were present in 90% of children less than 5 years old, in 71% of 5-10-year-olds, and in 50% of 10-15-year-olds. In Britons with type 1 diabetes, IAA were identified in 83% of children less than 10 years old and in 56% of children 10 years old and greater.

IAA have been detected in several other autoimmune diseases. IAA were identified in 15.9% of patients with Hashimoto's thyroiditis and 13.5% of Graves' disease subjects. In another study, IAA frequencies in various thyroid autoimmune diseases were 44% in Graves' disease, 21% in primary hypothyroidism, and 23% in chronic autoimmune thyroiditis, compared with 40% in primary adrenal failure, 36% in chronic hepatitis, 40% in pernicious anemia, 25% in rheumatoid arthritis, and 29% in systemic lupus erythematosus.

Approximately 2-3% of the general population express GAD autoantibodies. These antibodies are detected in 60% or more of new-onset cases of type 1 diabetes. The IA-2A and IA-213A general population frequencies are similar to GADA at 2-3%. IA-2A and IA-213A are observed in 60% or more of new-onset type 1 diabetes cases.

Early biochemical evidence of beta cell injury is a decreased first-phase insulin response to the administration of intravenous glucose (IVGTT). First-phase response is defined as the insulin concentrations at +1 and +3 min following completion of an intravenous bolus injection of glucose (e.g., 0.5 g/kg). There is also a dissociation in beta cell response to secretagogues: Initially the insulin response to intravenous amino acid administration (e.g., arginine) is preserved even while first-phase responses are deficient (Ganda, O. P. et al., 1984. "Differential sensitivity to beta-cell secretagogues in early, type 1 diabetes mellitus," *Diabetes* 33: 516-521). In ICA-positive individuals eventually developing insulin-dependent diabetes, first-phase insulin release diminishes at a rate of about 20-40 µU/mL/year (Srikanta, S. 1984. "Pre-type 1 diabetes, linear loss of beta cell response to intravenous glucose," *Diabetes* 33: 717-720).

When beta cell mass has substantially declined to less than 50% but more than 10% of normal, the OGTT may display abnormalities such as impaired fasting glucose (110-125 mg/dL) or impaired glucose tolerance (2-h glucose post-75-g challenge: 140-199 mg/dL). An abnormal OGTT prior to the clinical onset of type 1 diabetes is more likely observed in younger children. Frank clinical diabetes usually follows within 1-2 years of the onset of oral glucose intolerance. By the time acute symptoms of type 1 diabetes develop, beta cell mass is believed to have declined by approximately 90% or more from baseline. In one embodiment of the subject invention, treatment is administered once oral glucose intolerance is observed.

Most current procedures for the prediction of type 1 diabetes involve analyses of multiple islet autoantibodies. In every such study reported, nondiabetic individuals who express combinations of islet autoantibodies are found to be at greater risk for type 1 diabetes than individuals who express fewer varieties of islet autoantibodies. In addition, the total number of types of islet autoantibodies is usually more important than the specific combination of islet autoantibodies. In type 1 diabetes subjects, islet autoantibodies can also reappear after pancreas or islet transplantation, predicting failure to become insulin-independent (Bosi, E. et al. 2001. *Diabetes* 50:2464-2471).

Thus, in genetically predisposed individuals, an environmental trigger or triggers are believed to initiate beta cell autoimmunity, which can be identified by the presence of islet autoantibodies. With progressive beta cell damage, there is loss of first-phase insulin response to intravenous glucose administration. Subsequently the OGTT becomes abnormal, followed by symptoms of diabetes and the diagnosis of type 1 diabetes. Clearly the detection of islet autoimmunity can therefore be used as a predictive marker for the subsequent development of type 1 diabetes.

Both in nondiabetic relatives of type 1 diabetes subjects and in the general population, the detection of islet autoantibodies identifies individuals who are at high risk to develop subsequent type 1 diabetes (LaGasse, J. M. et al. 2002. *Diabetes Care* 25:505-511). Higher titers of ICA are more predictive than lower titers, and multiple islet autoantibodies are more powerful predictors than the presence of single autoantibodies. The combination of ICA plus low first-phase insulin secretion is possibly the strongest confirmed predictor of subsequent type 1 diabetes as demonstrated in the DPT-1. When using single autoantibodies, comparative sensitivities for the prediction of type 1 diabetes are as follows: ICA>GADA>IA-2A>>IAA. Combination islet autoantibody assays (e.g., the simultaneous detection of GADA and IA-2A (Sacks, D. B. et al. 2001. *J. Clin. Chem.* 47:803-804; Kawasaki, E. et al. 2000. *Front Biosci.* 5:E181-E190) will likely supersede ICA testing in future testing programs.

The majority of individuals with type 1 diabetes have islet autoantibodies at the time of onset of the disease. In cases where it is difficult to differentiate type 1 from type 2 diabetes, the presence of one or more islet autoantibodies (e.g., ICA, IAA, GADA, or IA-2A) is diagnostic of type 1a, immune-mediated diabetes (Rubinstein, P. et al. 1981. *Hum. Immunol.* 3:271-275). When individuals clinically present with a subtle, non-gketotic form of diabetes that may not be insulin-requiring yet are islet autoantibody-positive, LADA is diagnosed.

Materials and Methods
Animals, Stool Sampling, and DNA Extraction

Two experiments were conducted with two independent sets of rats. In experiments 1 and 2, three and ten rats of each genotype were used, respectively. Stool samples were collected at 20, 30, and 70 days after birth. The genotypes were the bio-breeding diabetes-resistant (BB-DR) and the bio-breeding diabetes-prone (BB-DP) rats. In BB-DP rats, the onset of diabetes begins at 70 days. For animal housing, AALAC standards were used with 4 males or five females per cage under pathogen-free conditions. BB-DR and BB-DP rats were kept in separate cages but all rats were in the same room at the same temperature and light. All rats received the same water and food. All animals were put into an individual cage for the stool collection for about 4-5 hours to eliminate contamination from the stool of other animals. Rats were housed and samples obtained from Biomedical Research Models, Inc. (Worcester, Mass., USA).

After storage at −20° C. until DNA extraction, bacterial DNA was isolated from the stool samples using the FastDNA® Kit (Qbiogene Inc., Carlsbad, Calif.). After the DNA extraction, samples were purified with the DNeasy Tissue kit (Qiagen, Valencia, Calif.) following the manufacturer's instructions.

ARISA Analysis

Bacterial community composition was assessed by Automated Ribosomal Intergenic Spacer Analysis (ARISA), a culture-independent technique for constructing bacterial community fingerprints based on the length heterogeneity of the intergenic transcribed spacer region of bacterial rRNA operons (Fisher and Triplett, 1999; Bosshard et al., 2000). ARISA was modified by separating PCR products on a chip with an Agilent Bioanalyzer 2100 (Agilent Technology, Santa Clara, Calif.). In this study, ARISA profiles were assumed to be indicative of bacterial community composition, and differences in ARISA profiles were assumed to reflect variation in the composition of the respective bacterial communities.

PCR reaction was performed with the GOTAQ® PCR core system (Promega, Madison Wis.). The mixtures contained 5 µl of 10×PCR buffer, 200 µM dNTPs, 100 µM of each primer, 2.5 U of Taq polymerase, and approximately 100 ng of DNA template in a final volume of 50 µl. The primers used were S-D-Bact-1522-b-S-20 and L-D-Bact-132-a-A-18 (Ranjard et al., 2001). Reaction mixtures were held at 94° C. for 3 min, followed by 30 cycles of amplification at 94° C. for 45 s, 55° C. for 1 min., and 72° C. for 2 min. and a final extension of 72° C. for 7 min.

ARISA PCR products were purified with the QIAquick PCR Purification Kit (Qiagen, Valencia, Calif.). The amplification products fragments were then resolved by on-chip gel electrophoresis with an Agilent 2100 Bioanalyzer and the DNA LABCHIP® Kit 7500 (Agilent Technology, Santa Clara, Calif.). Size standards were also resolved in separate wells to estimate the size of each PCR product. The data were translated into gel-like images where peaks from the electropherograms are translated to appear as bands on a gel (FIG. 1). For each ARISA data set, the size, number, and area of peaks in the electropherograms were used to compare samples. Area peaks were standardized by dividing each single area peak by the total area of the peaks in the same sample.

To assess the degree of similarity among the samples, bacterial diversity and richness were calculated based on ARISA profiles. The bacterial diversity was estimated by using Shannon-Weaver index (H=sum ($P_i$ ln [$P_i$]) where $P_i$ is the number of a given species divided by the total number of species observed). The richness was estimated by using Margalef's index (d=(S−1)/log N) where S is the total number of species and N is the total number of individuals in the sample which provides a measure of species richness that is roughly normalized for sample size.

The Bray-Curtis similarity index was calculated to assess the degree of similarity among the samples and produce a similarity matrix. The resulting matrices with pairwise similarities were used to group samples that represented similar bacterial community composition. Hierarchical clustering was calculated by using complete linkage algorithm and the results were represented by a dendrogram with the x axis representing the full set of samples and the y axis defining a similarity level at which two samples were considered to have fused. All data analysis for the ARISA bands was conducted using the software PRIMER 6 version. 6.1.9 (PRIMER-E Ltd, Lutton, UK).

To identify the bacteria represented within specific ARISA bands, the PCR products were resolved on a 1.2% agarose gel and the appropriate bands excised. The bands were purified using the QIAEX® II Gel Extraction Kit (Qiagen, Valencia, Calif.). The purified fragments were cloned into a TOPO TA Cloning® (Invitrogen, Carlsbad, Calif.). Plasmids were purified with the QIAprep spin miniprep Kit (Qiagen, Valencia, Calif.) and the DNA fragments were cycle sequenced in both directions with T7 and T3 primers using DYEnamic ET terminator cycle sequencing kit (GE Healthcare), on a PTC200 thermocycler (BioRad) and run on a 96 well MegaBACE 1000 capilarity sequencer (GE Healthcare).

Vector sequence present in each sequence was eliminated using VecScreen. After elimination of potentially chimeric sequences, the nucleotide sequences were compared to all sequences in the NCBI database using Megablast (Altschul et al. 1997). Bacterial taxonomic affiliations were assigned based on the closest NCBI match. The criteria to assign a sequence to its closest relative were based on the best e-value (greater than 1e-50) and on the best bit-score (greater than 200). Sequences that did not match this criterion remained unclassified.

16S rRNA Gene Amplification, Cloning, and Sequencing

A fragment of 16S rRNA gene was amplified from the 60-day samples in order to confirm that the bacterial communities in both rat lines had differentiated by that time. To amplify the 16S rRNA gene fragments, primers 787f and 1492r were chosen (Roesch et al., 2007). The PCR conditions used were 94° C. for 2 minutes, 30 cycles of 94° C., 45s denaturation; 55° C., 45s annealing; and 72° C., 1 min extension; followed by 72° C. for 6 minutes. The PCR products were cleaned, cloned into TOPO TA Cloning®, purified, sequenced, and sequences trimmed as described above. The sequences were aligned using ClustalX 1.83 (Thompson et al., 1997). Both weighted and unweighted UniFrac (Lozupone et al., 2006) were used to perform a Principal Coordinates Analysis (PCA) to find clusters of small groups of samples. The 16S rRNA gene sequences were classified using a Megablast search using the RDP II database. GenBank accession numbers EU812993 to EU814325 have been assigned to the DNA sequences obtained in this work.

16S rRNA Gene Amplification and Pyrosequencing

A fragment of 16S rRNA gene from the V9 region was amplified from the DNA extracted from the stool samples. We amplified the 16S rRNA gene fragments using the primers 787f and a modification of 1492r (Roesch et al., 2007). The primers were attached to the 454 LIFE SCI- ENCES® primer B and A (454 Life Sciences Corp., Branford, Conn.). The 454 run were multiplexed to obtain 16S rRNA sequences from twenty samples simultaneously. To do this, 8-base barcodes were added to the 5'-end of the reverse primers using the self-correcting barcode method of Hamady et al. (2008). For a list of primers and barcodes used see supplementary information. Six independent PCR reactions were performed for each sample. The PCR conditions used were 94° C. for 2 minutes, 25 cycles of 94° C., 45s denaturation; 55° C., 45s annealing; and 72° C., 1 min extension; followed by 72° C. for 6 minutes. The six PCR replications for each of 20 samples were combined and purified with the QIAquick PCR Purification Kit (Qiagen, Valencia, Calif.). The DNA concentration of the PCR product was then quantified by using on-chip gel electrophoresis with Agilent 2100 Bioanalyzer and DNA LABCHIP® Kit 7500 (Agilent Technology, Santa Clara, Calif.). Finally the reactions were combined in equimolar ratios to create a DNA pool that was used for pyrosequencing with primer B. The sequencing library was produced using the standard GS FLX library preparation procedure and two titration runs were performed. The average read length obtained was 215 bases. The maximum read length was 292. All reads were generated by GS FLX. All reads shorter than 100 were deleted from the analysis. The pyrosequences are deposited in GenBank as accession numbers FJ269364-FJ291326 and FJ291327-FJ313064 for the diabetes-prone sequences and FJ313065-FJ345302 for the diabetes-resistant sequences.

Data Preparation Prior to Further Analysis

Initially, all pyrosequencing reads were screened for quality and length of the sequences. The ends of the sequences that presented a Phred score smaller than 20 were trimmed and those reads that were shorter than 100 bases were removed from the dataset by using a program called Trim2 (Huang et al., 2006). The trimmed sequences were than screened for the 8-base barcode. A custom perl script was written to find the barcode and generate a new file for each sample. The sequences were then relabeled to denote the original sample.

Library Comparisons

Figures 1, 2B:
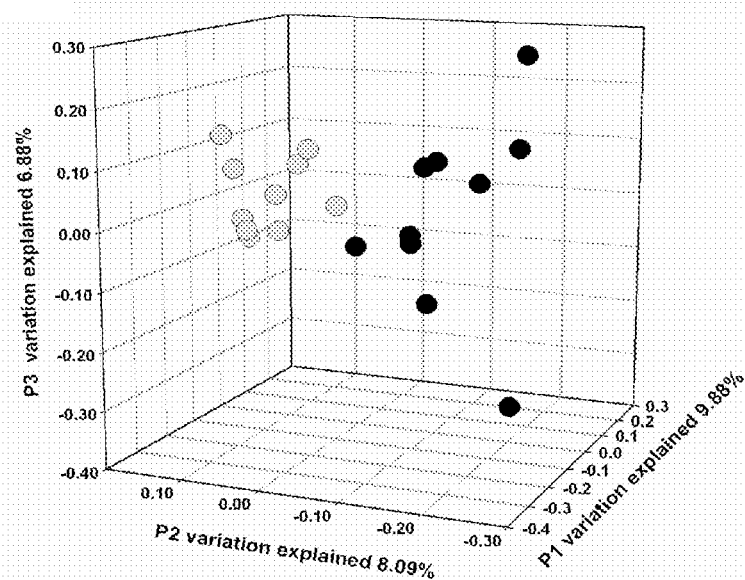
Figures 2, 2B:
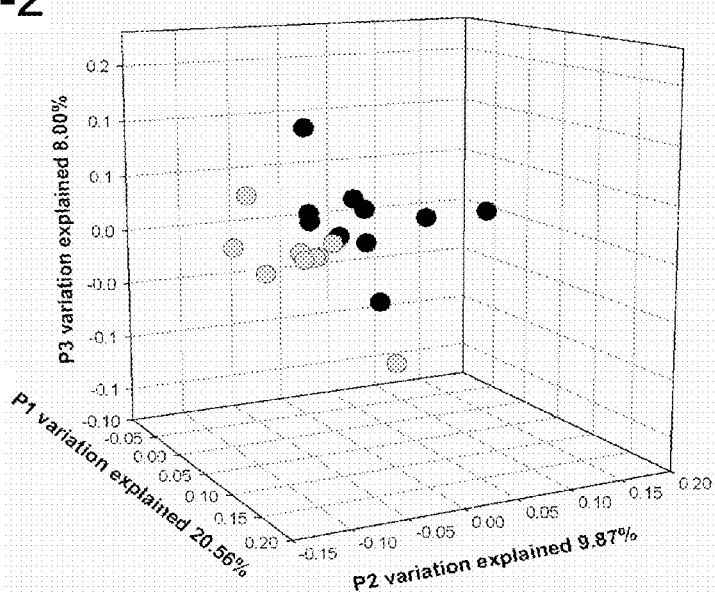

For the overall comparison for significant differences among the bacterial communities evaluated, we first group the sequences from each sample into Operational Taxonomy Units (OTU's) (cutoff value for assigning a sequence to the same group was equal or greater than 97% similarity) using the program CD-HIT (Li and Godzik, 2006). Representative sequences (the longest sequence of the cluster) were chosen and merged in a single file. This file was used as input for MUSCLE (Edgar, 2004), which built a guide tree using UPGMA (Unweighted Pair Group Method with Arithmatic Mean) agglomerative clustering method. Quantitative and qualitative bacterial diversity measures were done using UniFrac (Lozupone et al., 2006). Unifrac analysis required a phylogenetic tree prepared using MUSCLE and the number of sequences found on each OTU in each sample. To assess the qualitative and quantitative diversity of the bacterial communities unweighted and weighted UniFrac were used, respectively. Unifrac Principal Coordinates Analysis (PCA) was performed in order to find clusters of similar groups of samples. PCA is an ordination method based on multivariate statistical analysis that maps the samples in different dimensions and reflects the similarity of the biological communities. A matrix using the UniFrac metric for each pair of environments is calculated. The distances are turned into points in space with the number of dimensions one less than the number of samples. The first three principal dimensions were used to plot a 3-dimensional graph (FIG. 2).

Similarity Among Communities Based on Membership and Structure

In order to identify the organisms whose abundance differs between the BB-DP and BB-DR samples, sequence libraries were combined and each sequence was assigned to an Operational Taxonomic Unit (OTU) at 95% and 97% similarity by using CD-HIT (Li and Godzik, 2006). The number of sequences in each OTU found in each sample was used to construct a table with OTU's (lines) and samples (columns). This operation was performed by using a custom script written in PHP/HTML. The script uses as input the .clstr file from CD-HIT. The input data is stored in a database were the data is organized in two columns. The first column represents the sample name and the second represents the OTU number. Using mysql statements all the data contained for each OTU is collected and compared with an array that contains all of the sample names. The list grows with each new match found. After all comparisons are finished, all OTUs are phylogenetically classified.

Phylogenetic Classification of 16S rRNA Gene Fragments

The 16S rRNA gene sequences were phylogenetically classified using blast searches against the RDP II database. The closest bacterial relatives were assigned according to their best matches to sequences in the database using an e-value threshold equal to or less than $10^{-20}$ and a bit score equal to or greater than 200.

To determine whether specific bacterial genera or species differed between BB-DP and BB-DR rats, an exact Chi-square test (based on 50000 Monte Carlo iterations) was performed to get a p-value for the null hypothesis that there was no difference between the resistant and prone rats. The exact test, which is based on permutations, is not sensitive to zero counts in the bacterial relatives. The p-values were ordered and processed to find a false discover rate (FDR) cutoff of 1%.

Real-Time Quantification of Total *Bifidobacterium* and *Lactobacillus* Load

The DNA extracts were each used as a template for two separated PCRs using primers first described by Delroisse et al. (2006). The primers used are F-lacto (5'-gaggcagcag-tagggaatcttc-3' (SEQ ID NO:1)), R-lacto (5'-ggccagttactac-ctctatccttcttc-3' (SEQ ID NO:2)), F-bifido (5'-cgcgtcyggtgt-gaaag-3' (SEQ ID NO:3)) and R-bifido (5'-ccccacatccagcatcca-3' (SEQ ID NO:4)). Quantitative PCRs were performed in a reaction volume of 20 ul containing 1× Fast Start Sybr Green Master Mix (Roche Diagnostics, Indiana, USA), 200 nM each forward and reverse primers, and 5 ng of DNA extracted from the stool samples. Amplification and detection of DNA were performed with the iCycler detection system (BioRad) with optical grade 96-well PCR plates and optical film. The reaction conditions were 50° C. for 2 min and 95° C. for 10 min, followed by 45 cycles of 95° C. for 15 s and 62° C. for 1 min. Data analysis was conducted with the software supplied by Bio-Rad. Purified genomic DNA in the range 10 fg to 1 ng of *Lactobacillus reuteri* were used as the standard for determining the amount of *Lactobacillus* or *Bifidobacterium* DNA by real-time PCR. Using *L. reuteri* DNA as a standard for both genera is appropriate given that both have similar genome sizes. DNA concentrations were determined with the Nanodrop™ spectrophotometer.

Calculation of Bacterial Cell Numbers Following Quantitative PCR

The conversion of the amount of *Lactobacillus* and *Bifidobacterium* DNA into cell numbers in the stool samples was determined as described by Byun et al. (2004). In this method, an average genome size of 2.2 Mb is assumed along with similar 16S rRNA gene copy numbers (Klaenhammer et al., 2002; Makarova et al., 2006). With these parameters, each cell is assumed to contain approximately 2.4 fg of DNA (Byun et al., 2004).

Primers and Barcode Sequences Used
Forward Primer

The underlined sequence is 454 Life Sciences® primer B, and the bold sequence is the bacterial primer 787f. The TC, in italics, is a two-base linker sequence that helps to mitigate any effect the composite primer might have on PCR efficiency.

(SEQ ID NO: 5)
B-5'-<u>GCCTTGCCAGCCCGCTCAGT</u>*C*ATTAGATACCCNGGTAG-3'

Reverse Primer

The underlined sequence is 454 Life Sciences® primer A, and the bold sequence is the bacterial primer 1492r. The next eight-base sequence designates the barcode and the "TC", in italic, is a linker between the barcode and rRNA primer that helps to mitigate any effect the composite primer might have on PCR efficiency.

(SEQ ID NO: 6)
A1-5'-<u>GCCTCCCTCGCGCCATCAG</u>AAGCCGTTT*C*GNTACCTTGTTACGACTT-3'

(SEQ ID NO: 7)
A2-5'-<u>GCCTCCCTCGCGCCATCAG</u>ACACACAC*TC*GNTACCTTGTTACGACTT-3'

(SEQ ID NO: 8)
A3-5'-<u>GCCTCCCTCGCGCCATCAG</u>AGACACAGT*C*GNTACCTTGTTACGACTT-3'

(SEQ ID NO: 9)
A4-5'-<u>GCCTCCCTCGCGCCATCAG</u>ATAACCGCT*C*GNTACCTTGTTACGACTT-3'

(SEQ ID NO: 10)
A55'-<u>GCCTCCCTCGCGCCATCAG</u>CAACACCAT*C*GNTACCTTGTTACGACTT-3'

(SEQ ID NO: 11)
A6-5'-<u>GCCTCCCTCGCGCCATCAG</u>CCAACCAAT*C*GNTACCTTGTTACGACTT-3'

(SEQ ID NO: 12)
A7-5'-<u>GCCTCCCTCGCGCCATCAG</u>CGAACCATT*C*GNTACCTTGTTACGACTT-3'

(SEQ ID NO: 13)
A8-5'-<u>GCCTCCCTCGCGCCATCAG</u>CTACACCTT*C*GNTACCTTGTTACGACTT-3'

(SEQ ID NO: 14)
A9-5'-<u>GCCTCCCTCGCGCCATCAG</u>GAACACCTT*C*GNTACCTTGTTACGACTT-3'

(SEQ ID NO: 15)
A10-5'-<u>GCCTCCCTCGCGCCATCAG</u>GCAACCAT*TC*GNTACCTTGTTACGACTT-3'

(SEQ ID NO: 16)
A11-5'-<u>GCCTCCCTCGCGCCATCAG</u>GGAACCAA*TC*GNTACCTTGTTACGACTT-3'

(SEQ ID NO: 17)
A12-5'-<u>GCCTCCCTCGCGCCATCAG</u>GTACACCA*TC*GNTACCTTGTTACGACTT-3'

(SEQ ID NO: 18)
A13-5'-<u>GCCTCCCTCGCGCCATCAG</u>TAATCCGG*TC*GNTACCTTGTTACGACTT-3'

(SEQ ID NO: 19)
A14-5'-<u>GCCTCCCTCGCGCCATCAG</u>TCACACAG*TC*GNTACCTTGTTACGACTT-3'

(SEQ ID NO: 20)
A15-5'-<u>GCCTCCCTCGCGCCATCAG</u>TGACACAC*TC*GNTACCTTGTTACGACTT-3'

(SEQ ID NO: 21)
A16-5'-<u>GCCTCCCTCGCGCCATCAG</u>TTAACCGG*TC*GNTACCTTGTTACGACTT-3'

(SEQ ID NO: 22)
A17-5'-<u>GCCTCCCTCGCGCCATCAG</u>AAGGATCG*TC*GNTACCTTGTTACGACTT-3'

(SEQ ID NO: 23)
A18-5'-<u>GCCTCCCTCGCGCCATCAG</u>ACCATGCA*TC*GNTACCTTGTTACGACTT-3'

(SEQ ID NO: 24)
A19-5'-<u>GCCTCCCTCGCGCCATCAG</u>AGACAGTG*TC*GNTACCTTGTTACGACTT-3'

(SEQ ID NO: 25)
A20-5'-<u>GCCTCCCTCGCGCCATCAG</u>CAACTGCA*TC*GNTACCTTGTTACGACTT-3'

Figure 5:
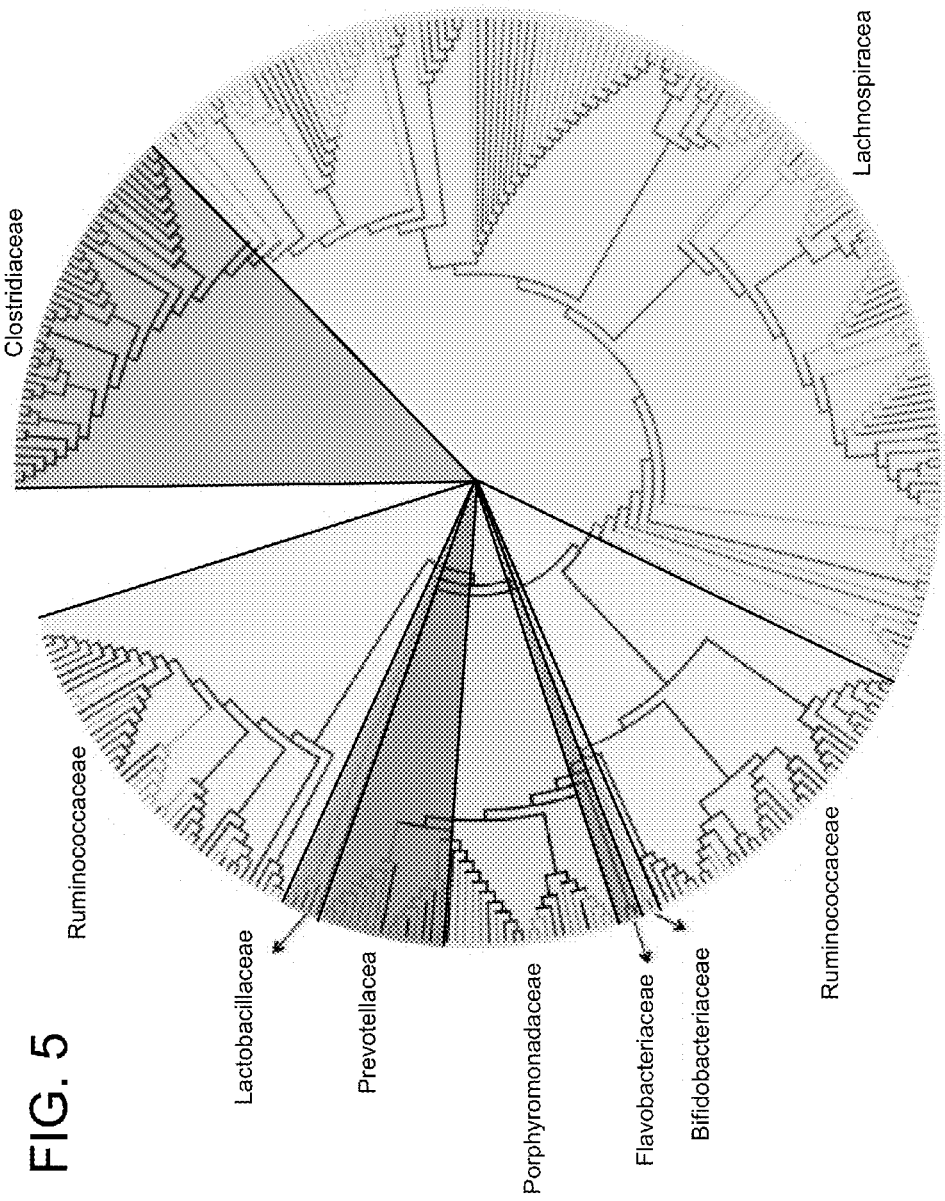
FIG. 5 shows the family-level phylogenetic classification of those OTUs that could not be classified at the genus or species levels. Red branches depict 16S rRNA sequences from BB-DP rats and green branches depict sequences from BB-DR. Branches in black depict known sequences from bacterial isolates. A list of bacterial isolates that were aligned with the sequences obtained from this study can be seen in the supplementary material. Sequences were aligned by using NAST (DeSantis et al., 2006). The aligned sequences and their respective nearest-isolates were uploaded in MEGA 4 (Tamura et al., 2007) for conduction of the phylogenetic analysis. The evolutionary history was inferred using the neighbor-Joining method and the evolutionary distances were computed using the Maximum Composite Likelihood method. All positions containing gaps and missing data were eliminated from the dataset (Complete deletion option). Striking taxonomic trends were observed with the Clostridiaceae and Ruminococcaceae more prevalent in BB-DP while the Lachnospiraceae, Porphyromonadaceae, and Prevotellaceae were more common in BB-DR.

Following is a list of near-neighbors bacterial isolates presented in FIG. 5 that were used to construct the phylogeny with the unclassified 16S rRNA sequences. The accession number in the Gene Bank precedes the isolate's name.

AAVC01000013.1 *Clostridium cellulolyticum* str. H10
AAV002000010.1 *Ruminococcus obeum* str. ATCC 29174
AB021701.1 *Mogibacterium pumilum* str. ATCC 700696
AB053941.1 *Tannerella forsythensis* str. HG3
AB053942.1 *Tannerella forsythensis* str. KM3
AB075772.1 *Clostridium sphenoides* str. ATCC 19403
AB093546.1 *Clostridium* sp. str. JC3
AB100838.1 *Heliorestis baculata* str. DSM 13446
AB117566.1 *Clostridium hylemonae* str. CT-9
AB158767.1 *Lactobacillus vaginalis* str. MF2123
AB238922.1 *Parabacteroides distasonis* str. JCM 5825
AB244773.1 *Prevotella copri* str. CB28
AB370251.1 *Barnesiella intestinihominis* str. YIT 11860
ABFK02000017.1 *Alistipes putredinis*str. DSM 17216
ABGD02000031.1 *Anaerotruncus colihominis* str. DSM 17241
AF016691.1 *Acidaminobacter hydrogenoformans* str. glu 65
AF028349.1 *Clostridium fusiformis* CM973
AF030449.1 *Ruminococcus flavefaciens* str. ATCC 49949; C52
AF030451.1 *Ruminococcus albus* str. ATCC 27211; 20
AF079102.1 *Heliorestis daurensis* str. BT-H1
AF092549.1 *Clostridium algidixylanolyticum* str. SPL73
AF126687.1 *Clostridium fimetarium* str. Z-2189; DSM 9179
AF157050.1 *Lactobacillus* sp. ASF360 str. ASF 360
AF202262.1 *Pseudobutyrivibrio ruminis* str. pC-XS7
AF202264.1 *Syntrophococcus sucromutans* str. S195
AF227870.1 *Bifidobacterium* sp. str. 65947
AF243154.1 *Lactobacillus vaginalis* str. KC19
AF262239.1 *Clostridium leptum* str. 10900
AF287759.1 *Bifidobacterium* sp. oral strain str. A32ED oral
AF319778.1 *Bacteroides* sp. str. 139
AF418173.1 *Desulfococcus multivorans* str. DSM 2059

AF481229.1 *Prevotella* sp. str. E9_42
AJ002591.1 *Clostridium* sp. str. DSM 10643 Lip1
AJ222546.1 *Anaerobacter polyendosporus*
AJ270469.2 *Faecalibacterium prausnitzii* str. A2-165
AJ311620.2 *Clostridium hathewayi* str. DSM 13479=CCUG 43
AJ318527.2 *Bryantella formatexigens* I-52
AJ413954.1 *Faecalibacterium prausnitzii* str. ATCC 27768
AJ428553.1 *Butyrivibrio hungatei* str. JK 615
AJ505973.1 *Bryantella formatexigens* I-52
AJ506115.1 *Clostridium estertheticum* subsp. laramiense str. DSM 14864 subsp.
AJ508452.1 *Clostridium bolteae* str. 16351
AM915269.1 *Ruminococcus flavefaciens* str. C94=ATCC 19208
AY136666.1 *Bacteroides capillosus* str. ATCC 29799
AY169414.1 *Lachnospira pectinoschiza*
AY169415.1 *Clostridium nexile*
AY169422.1 *Clostridium clostridioforme*
AY178843.1 *Pseudobutyrivibrio ruminis* str. Ce4
AY244776.1 *Haloanella gallinarum* str. 2002-2301269
AY331143.1 *Mahella australiensis* str. 50-1-BON
AY347530.1 *Butyrivibrio fibrisolvens* str. 0/10
AY353957.1 *Clostridium amygdalinum* str. BR-10
AY445598.1 *Ruminococcus flavefaciens* str. R13e2
AY518589.1 *Acetanaerobacterium elongatum* str. Z1
AY552788.2 *Clostridium hathewayi*
AY603000.2 *Thermoincola carboxydophila* str. 2204
AY643492.1 *Dysgonomonas wimpennyi* str. ANFA2
AY689228.1 *Prevotella nigrescens* str. ChDC KB6
AY689229.1 *Prevotella nigrescens* str. ChDC KB50
AY699273.1 *Butyrivibrio fibrisolvens* M55
AY699274.1 *Butyrivibrio fibrisolvens* L8
AY730663.1 *Clostridium orbiscindens* str. NML 00-082
AY804150.1 *Roseburia faecalis* str. M88/1
AY878326.1 *Clostridium scindens*
AY959944.2 *Clostridium alkalicellum* str. Z-7026
AY960568.1 *Anaerostipes*sp. str. 1E4
CP000139.1 *Bacteroides vulgatus* str. ATCC 8482
CP000139.1 *Bacteroides vulgatus* str. ATCC 8482
CP000140.1 *Parabacteroides distasonis* str. ATCC 8503
CP000141.1 *Carboxydothermus hydrogenoformans* str. Z-2901
CP000705.1 *Lactobacillus reuteri* F275 str. DSM 20016
D89329.1 *Bifidobacterium subtile* str. JCM 7109
D89330.1 *Bifidobacterium saeculare* str. DSM6533
DQ278862.1 *Clostridium aminophilum* 152R-1b
DQ358727.1 *Paenibacillus zanthoxylum* str. JH95
DQ882649.1 *Ruminococcus bromii* str. YE282
EF025906.1 *Clostridium coccoides* str. 8F
EF100911.1 *Caldicellulosiruptor kronotskiensis* str. 2902
EF408243.1 *Clostridium hathewayi*
EF533992.1 *Lactobacillus acidophilus* str. IDCC 3301
EF680276.1 *Clostridium thermocellum* str. JN4
EU109732.1 *Chryseobacterium*sp. str. B2
EU252503.1 *Dysgonomonas*sp. str. AM15
L09174.1 *Clostridium stercorarium*
L09175.1 *Clostridium sporogenes* str. RT51 B1
L35516.1 *Acetivibrio cellulolyticus*
M59083.1 *Acetitomaculum ruminis* str. 139B
NC_004193.1 *Oceanobacillus iheyensis* str. HTE831
NZ_AAV002000010.1 *Ruminococcus obeum* str. ATCC 29174
NZ_AAXA02000014.1 *Dorea formicigenerans* str. ATCC 27755
NZ_ABAX03000023.1 *Anaerostipes caccae* str. DSM 14662
NZ_ABFK02000017.1 *Alistipes putredinis* str. DSM 17216
U30147.1 *Lawsonia intracellularis* str. NCTC 12657
U77343.1 *Butyrivibrio fibrisolvens* str. OR79
X71846.1 *Clostridium aldrichii* str. DSM 6159
X71853.1 *Clostridium populeti* str. ATCC 35295
X73438.1 *Clostridium cellulovorans* str. DSM 3052
X73449.1 *Clostridium sphenoides* str. DSM 632
X75272.1 *Clostridium grantii*
X76161.1 *Clostridium aminobutyricum* str. DSM 2634
X76163.1 *Clostridium aerotolerans* str. DSM 5434
X76328.1 *Lactobacillus reuteri* str. DSM 20016 T
X76747.1 *Clostridium* sp str. DSM 6877(FS41)
X77839.1 *Clostridium polysaccharolyticum* str. DSM 1801
X77840.1 *Oxalophagus oxalicus* str. DSM 5503
X83430.1 *Ruminococcus flavefaciens* str. NCFB 2213
X85098.1 *Ruminococcus albus*
X85099.1 *Ruminococcus bromii*
X85100.1 *Ruminococcus callidus*
X87152.1 *Johnsonella ignava* str. ATCC 51276
X89973.1 *Butyrivibrio fibrisolvens* str. NCDO 2432
X89981.1 *Butyrivibrio crossotus* str. NCDO 2416
X94965.1 *Ruminococcus schinkii* str. B; CIP 105464; DSM 10518
X95893.1 *Pseudobutyrivibrio ruminis* str. DSM 9787
X96736.1 *Clostridium pascui* str. DSM 10365 (cm19)
Y10584.1 *Clostridium* sp. str. formate
Y11568.1 *Desulfotomaculum guttoideum* str. DSM 4024
Y11574.1 *Desulfotomaculum thermobenzoicum* str. DSM 6193
Y14581.1 *Oxalophagus oxalicus* str. DSM 5503T
Y18176.1 *Clostridium disporicum* str. DSM 5521
Y18180.1 *Clostridium thermosuccinogenes* str. DSM 5807
Y18185.1 *Clostridium saccharolyticum* str. DSM 2544
Y18186.1 *Clostridium scindens* str. DSM 5676
Y18214.1 *Desulfonispora thiosulfatigenes* str. DSM 11270
Y18530.1 *Dysgonomonas gadei* str. 1145589
Z49863.1 *Sporobacter termitidis* str. SYR Bacterial Strains Bacterial strains, *Lactobacillus johnsonii* N6.2 and *Lactobacillus reuteri* TD1, were isolated from BB-DR rats. Lactobacilli strains were grown in MRS (de Man, Rogosa and Sharpe) broth (REMEL, Lenexa, USA) at 37° C.

Analysis of the Intestinal Microflora by Real-Time Quantification

Viability counts were performed on samples taken from colonic content. Samples were immediately placed in 5 ml of sterile PBS buffer and viable counts for *Lactobacilli*, *Bacteroides*, anaerobes and enterobacteria were determined as described in Taranto et al. (2008), which is hereby incorporated by reference in its entirety.

For real-time quantification of microbial loads, DNA was extracted from samples preserved at −80° C. in RNAlater® solution (Ambion, Austin, Tex.), as described in Roesch et al. (2009), which is hereby incorporated by reference in its entirety. DNA extraction was performed using the QIAamp DNA Stool Mini kit (Qiagen Sciences, city, MD) following the manufacturer's instructions.

Selected groups of the rat fecal microbiota were measured using DNA extracts from each rat for RT-qPCR. Primer sequences for Real-time Quantification of microbial loads by RT-qPCR are based on the 16S rRNA, and are listed as follows.

| SEQ ID NO | TARGET | NAME | SEQUENCE | SOURCE |
|---|---|---|---|---|
| 26 | Bacteria | F_Bact 1369 | CGGTGAATACGTTCCCGG | 5 |
| 27 | | R_Prok 1492 | TACGGCTACCTTGTTACGACTT | |
| 28 | *Lactobacillus* | F-lacto | GAGGCAGCAGTAGGGAATCTTC | 6 |
| 29 | | R-lacto | GGCCAGTTACTACCTCTATCCTTCTTC | |
| 30 | *Bacteroides* | AllBac 296F | GAGAGGAAGGTCCCCCAC | 7 |
| 31 | | AllBac 412R | CGCTACTTGGCTGGTTCAG | |
| 32 | *Clostridium* | Ccoc 07 | GACGCCGCGTGAAGGA | 5 |
| 33 | | Ccoc 14 | AGCCCCAGCCTTTCACATC | |
| 34 | *Enterobacteriaceae* | En-lsu-3F | TGCCGTAACTTCGGGAGAAGGCA | 3 |
| 35 | | En-lsu-3R | TCAAGGACCAGTGTTCAGTGTC | |
| 36 | *Enterococcus* | g-Encoc-F | ATCAGAGGGGGATAACACTT | 3 |
| 37 | | g-Encoc-R | ACTCTCATCCTTGTTCTTCTC | |
| 38 | *Pseudomonas* | PSD7F | CAAAACTACTGAGCTAGAGTCG | 3 |
| 39 | | PSD7R | TAAGATCTCAAGGATCCCAACGGCT | |
| 40 | *Staphylococcus* | STPYF | ACGGTCTTGCTGTCACTTATA | 3 |
| 41 | | STPYR2 | TACACATATGTTCTTCCCTAATAA | |
| 42 | *Bifidobacterium* | F-bifido | CGCGTCYGGTGTGAAAG | 6 |
| 43 | | R-bifido | CCCCACATCCAGCATCCA | |

Quantitative PCR was performed with 1×iQ SYBR Green Supermix (Bio-Rad, Hercules, Calif.), 200 nM forward and reverse primers, and 5 ng of stool sample DNA. DNA concentrations were determined with the Nanodrop™ spectrophotometer. Amplification and detection of DNA were performed in duplicate with the iCycler detection system (BioRad). Reaction was performed under the following conditions: 50° C. for 2 min, 95° C. for 10 min, followed by 45 cycles of 95° C. for 15 sec and 62° C. for 1 min.

Data analysis was conducted with Bio-Rad software. DNA amplification standard curves were constructed using purified genomic DNA in the range 10 fg to 1 ng of *Lactobacillus reuteri, L. johnsonii, Staphylococcus* sp., *Bacteroides dorei* and *E. coli*, as described in Roesch et al. The conversion of DNA amounts into cell numbers was determined considering the genome size for each bacteria and the copy number of the 16S RNA gene, as described in Byun et al. (2004) and Matsuda et al. (2007), which are hereby incorporated by reference in their entirety.

Real-Time qPCR of Host Responses

DNA and RNA extractions from samples preserved at −80° C. in RNALATER® solution (Ambion, Austin, Tex.) were performed using the Ilustra™ TriplePrep kit (GE Health care, UK) following the manufacturer's instructions. cDNA was synthesized using iScript™ cDNA synthesis kit (Bio-Rad) and qRT-PCR were performed.

Primer sequences for host response by RT-qPCR are listed as follows.

| SEQ ID NO | TARGET | NAME | SEQUENCE | SOURCE |
|---|---|---|---|---|
| 44 | β-actin | β-actin Fw | TGACAGGTGCAGAAGGAGA | 8 |
| 45 | | β-actin Rv | TAGAGCCACCAATCCACACA | |
| 46 | Claudin-1 | Cldn-1_Fw | AGGTCTGGCGACATTAGTGG | 9 |
| 47 | | Cldn-1_Rv | TGGTGTTGGGTAAGAGGTTG | |

| SEQ ID NO | TARGET | NAME | SEQUENCE | SOURCE |
|---|---|---|---|---|
| 48 | Occludin | Occludin_Fw | GCTCAGGGAATATCCACCTATCA | 10 |
| 49 | | Occludin_Rv | CACAAAGTTTTAACTTCCCAGACG | |
| | Transforming Growth | | | |
| 50 | Factor-β | TGFB_Fw | GGACTACTACGCCAAAGAAG | 11 |
| 51 | | TGFB_Rv | TCAAAGACAGCCACTCAGG | |
| 52 | Interferon-γ | IFNγ_Fw | AGGATGCATTCATGAGCATCGCC | 12 |
| 53 | | IFNγ_Rv | CACCGACTCCTTTTCCGCTTCCT | |
| 54 | Tumor Necrosis | TNF-a_Fw | TCTTCTCATTCCTGCTCGTG | 13 |
| 55 | Factor-α | TNF-a_Rv | GATGAGAGGGAGCCCATTT | |
| | Inducible Nitric Oxide | | | |
| 56 | Synthase | iNOS_Fw | CTCACTGTGGCTGTGGTCACCTA | 8 |
| 57 | | iNOS_Rv | GGGTCTTCGGGCTTCAGGTTA | |
| 58 | Glutathione | GPX1_Fw | CGGTTTCCCGTGCAATCAGT | 14 |
| 59 | Peroxidase 1 | GPX1_Rv | ACACCGGGGACCAAATGATG | |
| 60 | Catalase | CAT_Fw | CGACCGAGGGATTCCAGATG | 14 |
| 61 | | CAT_Rv | ATCCGGGTCTTCCTGTGCAA | |
| 62 | Glutathione | GR_Fw | AGCCCACAGCGGAAGTCAAC | 14 |
| 63 | Reductase | GR_Rv | CAATGTAACCGGCACCCACA | |
| 64 | Superoxide | SOD1_Fw | GCGGTGAACCAGTTGTGGTG | 14 |
| 65 | Dismutase 1 | SOD1_Rv | AGCCACATTGCCCAGGTCTC | |
| 66 | Superoxide | SOD2_Fw | AGCTGCACCACAGCAAGCAC | 14 |
| 67 | Dismutase 2 | SOD2_Rv | TCCACCACCCTTAGGGCTCA | |
| 68 | Cyclooxygenase-2 | COX2_Fw | CTCTGCGATGCTCTTCCGAG | 15 |
| 69 | | COX2_Rv | AAGGATTTGCTGCATGGCTG | |
| | Indoleamine 2,3- | | | |
| 70 | Dioxygenase | IDO_Fw | GCTGCCTCCCATTCTGTCTT | 16 |
| 71 | | IDO_Rv | TGCGATTTCCACCATTAGAGAG | |

Intestinal Morphology

Intestinal injury was evaluated by histology. Neutral buffered formalin (10%, V/V) fixed ileum samples were embedded in paraffin, cut into 4 μm sections, mounted on glass slides, and stained with hematoxylin and eosin according to standard procedures. Villus height, width and crypt depth were measured using a Nikon microscope (Universal Imaging Corp., Westchester, Pa.) with an ocular micrometer.

The intestinal injury was evaluated using a semiquantitative scoring system ranging from 0 to 4 modified according to Arumugam et al. (2003), which is hereby incorporated by reference in its entirety. Normal mucosa was scored as grade 0. Epithelial cell damages, including loss of cells and separation of the epithelial cells from the underlying villus were scored between grades 1-3; while loss of villus tissue was scored as grade 4. Intestinal sections were also analyzed for goblet cells numbers per total cells within a villus. For each animal, counts from 6 villi for each slide in three different regions of the slide were averaged.

Western Blot Analysis of iNOS Expression

Protein expression was analyzed using whole cell lysates. Rat ileum samples were weighed, minced, and disaggregated by incubation at 250 rpm and 37° C. in PBS (1:2, w/v) with 0.25% collagenase. Samples were immediately placed on ice and homogenized by vortexing with glass beads (Sigma Life Science) containing Complete Mini Protease Inhibitor Cocktail (Roche, Mannheim, Germany). Samples were centrifuged at 13,000×g for 10 min at 4° C.

Protein concentration was determined by Bradford method (Bio-Rad Protein Assay). 40 ug of protein per sample was separated using sodium dodecyl sulfate-polyacrylamide electrophoresis and transferred onto Nitroplus membranes (MSI, Flanders, Mass.) using a semi-dry transfer method. Membranes were blocked for 1 hr in phosphate buffered saline with 0.075% tween 20 (T-PBS) and 5% milk. Membranes were incubated with mouse anti-iNOS antibody (1:1000) or mouse anti-β-actin (1:10,000) (Abcam, Cambridge, Mass.) in T-PBS at 4° C. overnight, and subsequently washed twice in T-PBS for five minutes. Incubation in horseradish peroxidase-conjugated anti-mouse antibody was performed for 1 hr and signal was detected using enhanced chemiluminescent system (Amersham Pharmacia Biotech). β-actin was utilized as an internal control.

Hexanoyl-Lys Enzyme-Linked Immunosorbent Assay

Relative lipid peroxidation was determined by analyzing hexanoyl-lys levels by ELISA on rat ileum cell suspensions. Twenty mg of each rat ileum sample was finely minced on a cold glass slide and suspended in 300 µl 1×PBS+0.25% collagenase type I (Invitrogen, Carlsbad, Calif.). Samples were vortexed vigorously at 5 min intervals while incubating at 37° C. for 30 min. Free-cell suspensions were separated from remaining connective tissue fractions after incubation.

Cell concentration was determined by optical density at 600 nm using a Syngery HT microplate reader (BioTek Instruments, Winooski, Vt.). Each sample was split into 1 ml aliquots (control and experimental sets), pelleted at 5000 rpm, and washed with 1 ml 1×PBS twice. Cell pellets were resuspended in 100 µl of 1×PBS. 100 µl of 1×PBS was added to the control set, and 100 µl of 1×PBS+2 µg/ml hexanoyl-lysine monoclonal antibody (JaICA, Shizuoka, Japan) was added to the experimental set. Samples were incubated at 37° C. for 1 h, followed by two washes in 1×PBS. 100 ul of 1×PBS+80 ng/ml of peroxidase labeled anti-mouse monoclonal antibody (Amersham Pharmacia Biotech, Pittsburgh, Pa.) was added to both sets and incubated for 1 hr at 37° C.

Following incubation, cells were washed twice and resuspended in 100 ul 1×PBS. A 20 mM reaction mixture of o-Phenylenediamine (Sigma, St. Louis, Mo.) was prepared in a 50 mM phosphate citrate buffer pH=5 and kept dark. Immediately before reading, 30% $H_2O_2$ was added to the reaction mixture to a final concentration of 0.04%. To each sample, 100 ul of reaction mixture was added, and samples were read continuously at 450 nm and 570 nm for 30 min using Syngery HT microplate reader (BioTek Instruments, Winooski, Vt.). Specific activity was calculated as the amount of product ($\mu mol \cdot min^{-1}$) and normalized for cell density. This assay was performed in triplicate for at least three animals in each group.

Statistical Analysis

Statistical analysis was performed utilizing the t-test for unpaired data or by the nonparametric Mann-Whitney. Differences with $P<0.05$ were considered significant. Data was analyzed by GraphPad Prism (GraphPad Software, San Diego, USA).

Following are examples which illustrate procedures for practicing the invention. These examples should not be construed as limiting. All percentages are by weight and all solvent mixture proportions are by volume unless otherwise noted.

Example 1—Direct Sequence Analysis of Arisa Bands

Two dominant peaks, 600 to 640 bp in size, were found in all the BB-DP samples but not in the BB-DR samples (FIG. 1). A dominant 370-bp peak was also found in all BB-DR samples that was not present among the stool samples from diabetes prone rats (FIG. 1). All three of these bands were excised from agarose gels and sequenced. A total of 247 sequences were obtained for the BB-DP specific 600- and 640-bp bands. The sequencing analysis showed that these bands were derived from strains of *Bacteroides*, *Xanthomonas* and *Acinetobacter*. The genera *Bacteroides* made up 44.9% of the sequences while *Xanthomonas* and *Acinetobacter* were found in 15.8 and 14.5% of the sequences tested, respectively. A total of 266 sequences were obtained for the 370-bp band that was BB-DR specific. *Lactobacillus* strains were the source of 92.8% of the sequences with the remaining sequences derived from *Clostridium*, *Flexibacter* and *Porphyromonas*. These results suggested that *Lactobacillus* may be more common in BB-DR than BB-DP and that *Bacteroides* may be more common in BB-DP.

Example 2—Comparison of the Bacterial Communities in Bb-Dr and Bb-DP Based on 16S rRNA Library Comparison An average of 138 16S rRNA sequences were obtained from the six stool samples from experiment 1. These sequences were aligned to prepare a distance matrix by calculating pairwise UniFrac values (Lozupone et al. 2006) for each BB-DP and BB-DR sample at 60 days of age. Principal coordinates analysis (PCA) of the matrix was constructed using UniFrac. As the number of OTUs are correlated with the amount of sampling effort (Hughes et al., 2001; Roesch et al., 2007), a simple comparison of the number of OTUs between groups can lead to misinterpretations due to undersampling or to variability between individuals rather than variability between groups. To avoid this problem, quantitative and qualitative bacterial diversity measures were calculated by using Principal Coordinates Analysis (PCA). This approach compares the communities for significant differences using phylogenetic information and multivariate statistical techniques for finding the most important axes along which the samples vary. In this study, PCA was also used to find clusters of samples that represent similar bacterial communities (FIG. 2).

PCA showed that the BB-DP communities were far more similar to each other than they were to any of the BB-DR communities (FIG. 2A). The BB-DP and BB-DR communities differed at the 1% level of confidence as measured using either weighted or unweighted UniFrac. Thus, the bacterial community composition differed whether or not the abundance of taxa was considered.

Example 3—Analysis of Bacterial Community Composition in Diabetes-Prone and Diabetes-Resistant Samples The results of experiment 1 encouraged a second experiment with more replicates per genotype and higher throughput 16S rRNA sequencing. The first analysis of the pyrosequencing data was to determine whether the bacterial communities found in the 20 rats at 70 days after birth differed significantly between the BB-DR and BB-DP rats. This was done by PCA as described above in experiment 1 (FIG. 2B).

Figure 3:
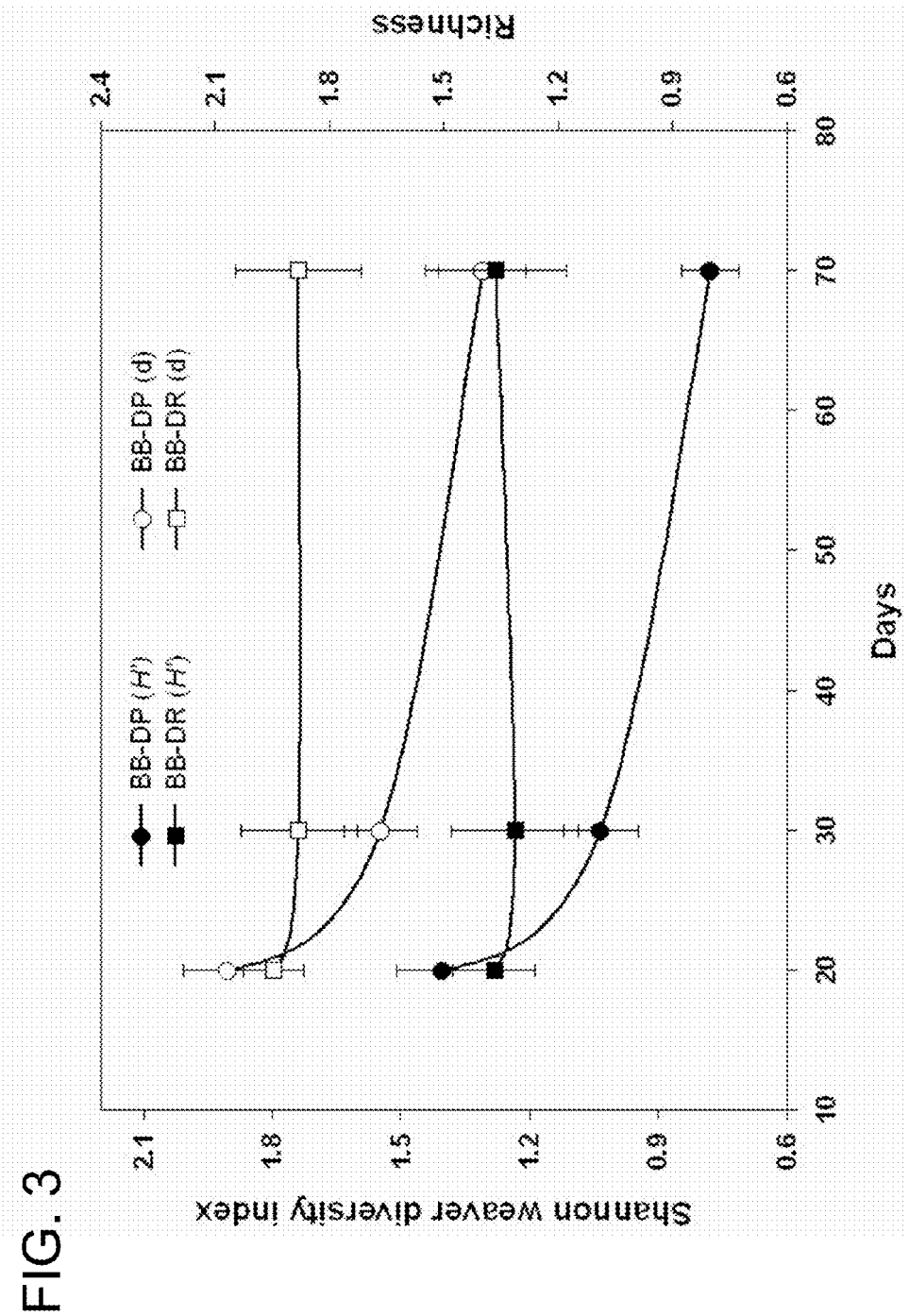
FIG. 3 shows the Shannon Weaver and richness diversity indices calculated for the three time points after birth when stool was collected. Circles and squares represent the BB-DP and BB-DR samples, respectively. Closed symbols represent the richness index (d) while open symbols depict the Shannon-Weaver (H') indices. Indices were calculated using ARISA data from the experiment 2 samples.

The weighted and unweighted UniFrac analyses showed that the bacterial community composition in the stool of diabetes-prone and diabetes-resistant rats was significantly different at the 1% level of confidence. The Shannon-Weaver and richness diversity indices were calculated for each time point in experiment 2 using the ARISA profiles (FIG. 3). The diversity indices did not change significantly over time in the BB-DR samples but did decline by 70 days in the BB-DP samples. There was no significant difference in diversity between the 20- and 30-day samples in B-EP or BB-DR.

Example 4—Identification of the Bacteria that Vary Between the Diabetes-Prone and Diabetes-Resistant Samples Having found statistically significant differences between bacterial communities in BB-DP and BB-DR rats (FIGS. 1 and 2), the next step was to identify those bacterial genera and species that were responsible for the differences observed. To determine the types of intestinal bacteria associated with TD1, we assigned the 16S rRNA sequences to closest bacterial relatives according to their best matches to sequences of known organisms by using BLAST search (Altschul, et al. 1997). Twenty 16S rRNA libraries were obtained by multiplex pyrosequencing and ranged in size from 1,261 to 7,997 sequences (Hamady et al. 2008; Table 4). Sequences within each library were compared and operational taxonomic units (OTUs) were identified using 95% or 97% similarity as criteria for assigning sequences to approximate the same genus or species, respectively. For the diabetes-prone samples, the number of operational taxonomic units (OTUs) at the 97% similarity level varied from 327 to 1,210 with an average of 748. For the diabetes-resistant samples, the number of OTUs varied from 270 to 1,689 with an average of 724.

The proportion of total reads that could be assigned to known genera was 22.33% and 23.65% of the BB-DP and BB-DR reads, respectively, using the 95% similarity level to define a genus. The proportion of total reads that could be assigned to known species was 12.06% and 13.23% of the BB-DP and BB-DR reads, respectively, using the 97% similarity level to define a species.

The bacterial communities were compared at the genus and species level with 74 bacterial genera and 124 bacterial species identified as inhabitants of the rat stools tested. To test which genera or species were different between resistant and prone rats, an exact Chi-square test showed that 24 bacterial species and 18 bacterial genera differed in abundance at the 1% level of confidence between diabetes-prone and diabetes-resistant samples (Tables 1 and 2). Those species and genera that did not differ are also presented (Tables 5 and 6). The most abundant genera found in these samples were *Clostridium* and *Bacteroides*. The abundance of the *Bacteroides* differed significantly between the diabetes-prone and diabetes-resistant samples while the clostridia did not change (Table S5). Five species of *Clostridium* were more abundant in BB-DP while one species was more abundant in BB-DR (Table 2).

Based on the exact Chi-square test, 9 genera were found to be statistically significantly higher in abundance in the BB-DP samples but statistically significantly lower in abundance or absent in the BB-DR samples (Table 1). Those genera were: *Bacteroides, Eubacterium, Halothermothrix, Ruminococcus, Anaerostripes, Mucispirillum, Butyrivibrio, Pediococcus,* and *Sporobacter*. Of these, *Bacteroides, Eubacterium* and *Ruminococcus* were the most abundant in the BB-DP samples with 6.73, 4.00, and 2.30%, respectively of the total number of sequences. In BB-DR rats, 9 bacterial genera were found in statistically greater numbers than in the BB-DP samples (Table 1). Those genera include *Bifidobacterium, Lactobacillus, Prevotella, Pseudobutyrivibrio, Spiroplasma, Proteiniphilum, Streptococcus, Turicibacter,* and *Bryantella*. Of these, the most abundant were *Lactobacillus, Bryantella, Bifidobacterium,* and *Turicibacter.*

The physiology of bacterial species within a genus can vary. Thus, species differences within each genus between the two rat genotypes were considered an important component of these analyses. At the 1% level of confidence, 24 bacterial species differed in abundance between the two rat genotypes (Table 2). Among them, 11 were more abundant in BB-DR and 13 were more abundant in BB-DP. Some of these differences were within a genus that did not differ between the two rat genotypes. For example, although the number of reads of *Clostridium* did not differ between the two treatments, 6 species of *Clostridium* did differ. Of these, 5 were more abundant in BB-DP while one species was more abundant in BB-DR (Table 2).

At the genus level, *Bacteroides* strains were more prevalent in BB-DP rats than in BB-DR. However, at the species level, strains of *B. capillosus, B. vulgatus* and *B. splanchnicus* were more common in BB-DP while *B. acidifaciens* and *B. massiliensis* strains were more common in BB-DR. Four *Lactobacillus* species were more common in BB-DR samples but unidentified Glade, L. sp., was more common in BB-DP.

Figure 4A:
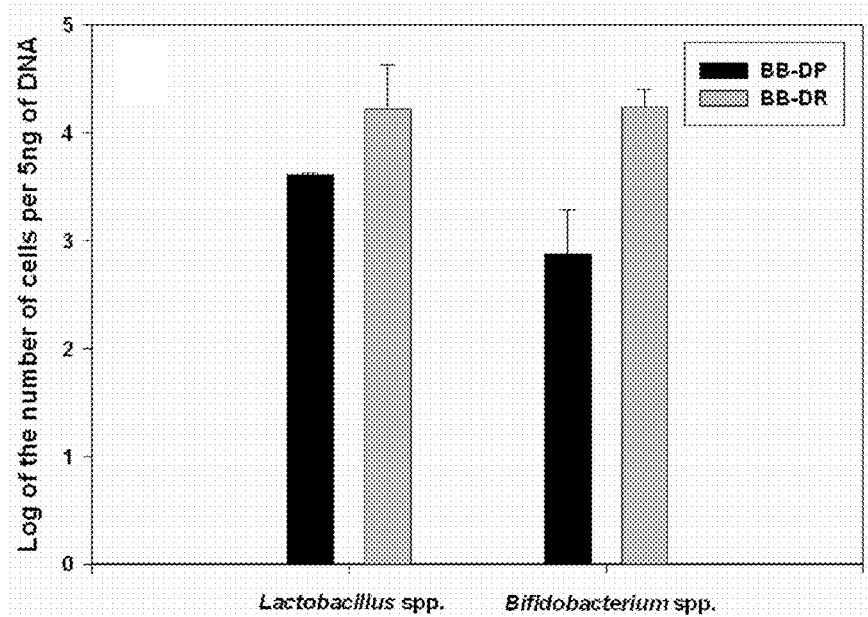
FIGS. 4A-4B show log of the number of *Lactobacillus* and *Bifidobacterium* cells per 5 ng of DNA from diabetes-resistant (BB-DR) and diabetes-prone (BB-DP) stool samples. 4A—experiment 1 (3 stool samples per genotype). 4B—experiment 2 (10 stool samples per genotype). The standard error about the mean is depicted in the error bar about the data columns.
Figure 4B:
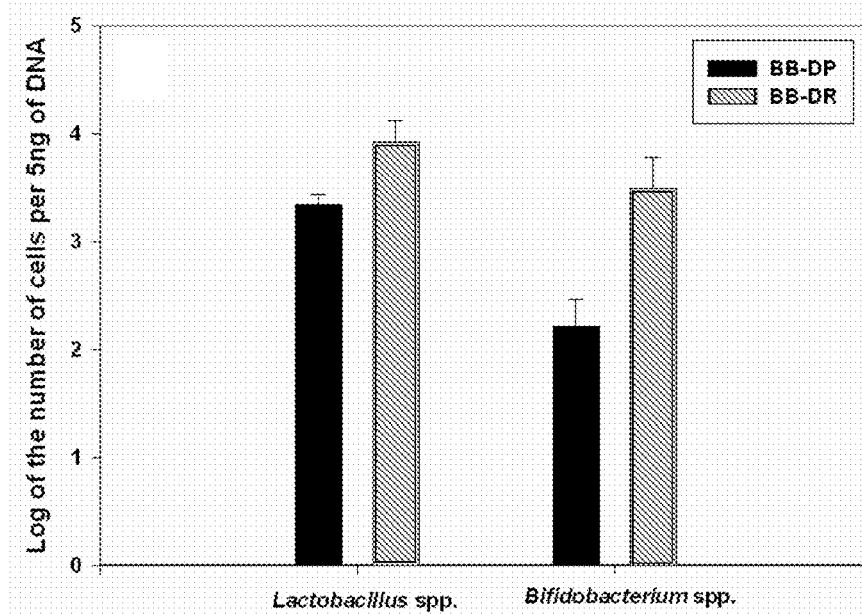

Example 5—Verification of the Pyrosequencing Results—Quantification of *Lactobacillus* and *Bifidobacterium* in the Diabetes-Prone and Diabetes-Resistant Samples In an attempt to verify the accuracy of the results obtained by using pyrosequencing, quantitative PCR was performed to quantify the abundance of two bacterial genera (*Lactobacillus* and *Bifidobacterium*) that are more common in BB-DR than in BB-DP samples. The Ct values obtained were converted into cell number and the averaged number of bacterial cells for the BB-DR and BB-DP samples (FIG. 4). Both genera were more common in BB-DR than in BB-DP samples confirming the pyrosequencing results.

The expression of bacterial abundance in qPCR experiments as cell numbers is well documented and accepted in the literature (Byun et al. 2004; Martin et al., 2006). In addition, an excellent correlation has been shown between *L. sakei* counts estimated by real-time PCR and *L. sakei* counts on MRS plates (FIG. 2, Table 3, Martin et al. 2004). In this report we used the same approach. Briefly, the conversion to cell numbers is based on a calibration curve in which a small fragment from the 16S rRNA gene specific to *Lactobacillus* or to *Bifidobacterium* is amplified. To this end, chromosomal DNA from either *Lactobacillus reuteri* (wild type isolate) or *Bifidobacterium* sp (wild type isolate) were quantified and serial dilutions were made. Different concentrations from 50 fg to 5 ng (20 to $2 \times 10^6$ genome equivalents) were used as a standard curve in the qPCR experiments.

Example 6—A Large Number of Sequences not Classified to the Genus Level

Most of the pyrosequences obtained could not be classified at the genus or species levels. Of those, 252 OTUs differed significantly between BB-DP and BB-DR. Of those, 139 were significantly more abundant in BB-DR while 113 where significantly higher in BB-DP. These organisms represented 24.4% and 21.4% of all reads in BB-DP and BB-DR, respectively. Of the 252 OTUs, 245 could be classified into five bacterial families: Clostridiaceae, Lachnospiraceae, Ruminococcaceae, Porphyromonadaceae, and Prevotellaceae (FIG. 5, Table 3). Of the 41 OTUs that differed between the two rat genotypes in the Clostridiaceae, 95% were more abundant in BB-DP than BB-DR. A similar trend was found in the Ruminococcaceae, where 67.9% of the 56 OTUs were more abundant in BB-DP than BB-DR. Conversely, of the 119 OTUs that differed between the two rat genotypes in the Lachnospiraceae, 77% were more abundant in BB-DR than BB-DP. The OTUs from Porphyromonadaceae and Prevotellaceae were also more likely to be in higher numbers in BB-DR than BB-DP.

TABLE 1

List of bacterial genera whose abundances differ statistically at the 1% level of confidence between the diabetes-resistant (BB-DR) and diabetes-prone (BB-DP) stool samples. The percent of total reads is shown for each genus. The percent of reads numbers in bold indicate the genotype (BB-DP or BB-DR), which is higher for that genus. Here a 16S rRNA sequence is considered to be derived from a known genus if it is at a similarity level of 95% or above to its closest cultured relative.

| Approximate genus level - 95% similarity to closest cultured relative | Phyla | % of all BB-DP reads | % of all BB-DR reads | p-value | Fold difference |
|---|---|---|---|---|---|
| Bacteroides | Bacteroidetes | 6.732 | 6.101 | 2.00E−05 | 1.5 |
| Bifidobacterium | Actinobacteria | 0.041 | 0.940 | 2.00E−05 | 16.8 |
| Eubacterium | Firmicutes | 4.009 | 2.050 | 2.00E−05 | 2.6 |
| Halothermothrix | Firmicutes | 0.126 | 0.003 | 2.00E−05 | 55.0 |
| Lactobacillus | Firmicutes | 5.320 | 8.012 | 2.00E−05 | 1.1 |
| Prevotella | Bacteroidetes | 0.307 | 0.630 | 2.00E−05 | 1.5 |
| Pseudobutyrivibrio | Firmicutes | 0.112 | 0.453 | 2.00E−05 | 3.0 |
| Ruminococcus | Firmicutes | 2.302 | 1.675 | 2.00E−05 | 1.9 |
| Spiroplasma | Mollicutes | 0.000 | 0.112 | 2.00E−05 | 36 |
| Anaerostipes | Firmicutes | 0.127 | 0.0523 | 0.000680 | 3.2 |
| Mucispirillum | Deferribacteres | 0.224 | 0.130 | 0.000760 | 2.3 |
| Butyrivibrio | Firmicutes | 0.030 | 0.000 | 0.000980 | 13 |
| Proteiniphilum | Bacteroidetes | 0.062 | 0.143 | 0.001420 | 1.7 |
| Streptococcus | Firmicutes | 0.025 | 0.081 | 0.001700 | 2.4 |
| Turicibacter | Firmicutes | 0.654 | 0.909 | 0.002040 | 1.2 |
| Pediococcus | Firmicutes | 0.032 | 0.003 | 0.003080 | 14 |
| Sporobacter | Firmicutes | 1.396 | 1.262 | 0.007040 | 1.5 |
| Bryantella | Firmicutes | 0.838 | 1.089 | 0.009580 | 1.4 |
| Total of % reads | | 22.334 | 23.645 | | |

TABLE 2

List of bacterial species whose abundance differs statistically at the 1% level of confidence between the diabetes-resistant (BB-DR) and diabetes-prone (BB-DP) stool samples. The percent of total reads obtained from BB-DP or BB-DR is shown for each species. The percent of reads numbers in bold indicate the genotype (BB-DP or BB-DR), which is higher for that genus. Here a 16S rRNA sequence is considered to be derived from a known species if it is at a similarity level of 97% or above to its closest cultured relative.

| Approximate species level - 97% similarity to closest cultured relative | Phyla | % BB-DP reads | % BB-DR reads | p-value |
|---|---|---|---|---|
| Bacteroides acidifaciens | Bacteroidetes | 0.119 | 0.437 | 2.00E−05 |
| Bacteroides capillosus | Bacteroidetes | 2.213 | 1.014 | 2.00E−05 |
| Bifidobacterium saeculare | Actinobacteria | 0.005 | 0.304 | 2.00E−05 |
| Clostridium aldrichii | Firmicutes | 0.126 | 0.034 | 2.00E−05 |
| Clostridium fimetarium | Firmicutes | 0.350 | 0.164 | 2.00E−05 |
| Clostridium nexile | Firmicutes | 0.320 | 0.199 | 2.00E−05 |
| Eubacterium siraeum | Firmicutes | 0.547 | 0.300 | 2.00E−05 |
| Eubacterium ventriosum | Firmicutes | 0.430 | 0.096 | 2.00E−05 |
| Lactobacillus frumenti | Firmicutes | 0.000 | 0.065 | 2.00E−05 |
| Lactobacillus intestinalis | Firmicutes | 0.597 | 1.967 | 2.00E−05 |
| Lactobacillus johnsonii | Firmicutes | 0.304 | 1.939 | 2.00E−05 |
| Prevotella marshii | Bacteroidetes | 0.229 | 0.493 | 2.00E−05 |
| Ruminococcus flavefaciens | Firmicutes | 0.339 | 0.158 | 2.00E−05 |
| Spiroplasma helicoides | Mollicutes | 0.000 | 0.111 | 2.00E−05 |
| Bacteroides vulgatus | Bacteroidetes | 0.492 | 0.338 | 6.00E−05 |
| Lactobacillus sp. | Firmicutes | 0.959 | 0.810 | 0.000120 |
| Mucispirillum schaedleri | Deferribacteres | 0.201 | 0.115 | 0.000400 |
| Bacteroides splanchnicus | Bacteroidetes | 0.030 | 0.000 | 0.001260 |
| Clostridium orbiscindens | Firmicutes | 0.222 | 0.143 | 0.001260 |
| Bacteroides massiliensis | Bacteroidetes | 0.135 | 0.258 | 0.002280 |
| Clostridium hylemonae | Firmicutes | 0.000 | 0.022 | 0.003660 |
| Clostridium glycolicum | Firmicutes | 1.558 | 1.511 | 0.005760 |

TABLE 2-continued

List of bacterial species whose abundance differs statistically at the 1% level of confidence between the diabetes-resistant (BB-DR) and diabetes-prone (BB-DP) stool samples. The percent of total reads obtained from BB-DP or BB-DR is shown for each species. The percent of reads numbers in bold indicate the genotype (BB-DP or BB-DR), which is higher for that genus. Here a 16S rRNA sequence is considered to be derived from a known species if it is at a similarity level of 97% or above to its closest cultured relative.

| Approximate species level - 97% similarity to closest cultured relative | Phyla | % BB-DP reads | % BB-DR reads | p-value |
|---|---|---|---|---|
| *Streptococcus oligofermentans* | Firmicutes | 0.021 | 0.065 | 0.008820 |
| *Lactobacillus acidifarinae* | Firmicutes | 0.000 | 0.019 | 0.009160 |
| % of total reads | | 9.1970 | 10.562 | |

TABLE 3

A large number of OTUs (252) differed significantly between BB-DR and BB-DP but could not be classified at the genus or species levels. The distribution of most (245) of these OTUs among five bacterial families is shown below.

| Family | no. in BB-DP | no. in BB-DR | Total | % BB-DP | % BB-DR |
|---|---|---|---|---|---|
| Clostridiaceae | 39 | 2 | 41 | 0.951 | 0.049 |
| Lachnospiraceae | 27 | 92 | 119 | 0.227 | 0.773 |
| Ruminococcaceae | 38 | 18 | 56 | 0.679 | 0.321 |
| Porphyromonadaceae | 5 | 13 | 18 | 0.278 | 0.722 |
| Prevotellaceae | 0 | 11 | 11 | 0.000 | 1.000 |
| Total | 109 | 136 | 245 | 0.445 | 0.555 |

TABLE 4

Number of pyrosequencing reads obtained from each sample and the number of operational taxonomic units (OTUs) observed in each sample at the 97% and 95% level of similarity.

| Sample | No. of pyrosequencing reads | OTUs observed Level of similarity | | Reads/OTU Level of similarity | |
|---|---|---|---|---|---|
| | | 95% | 97% | 95% | 97% |
| Diabetes Prone | | | | | |
| BB-DP-1 | 6,178 | 654 | 962 | 9.45 | 6.42 |
| BB-DP-2 | 7,101 | 714 | 1,059 | 9.95 | 6.71 |
| BB-DP-3 | 6,321 | 558 | 793 | 11.33 | 7.97 |
| BB-DP-4 | 4,573 | 475 | 702 | 9.63 | 6.51 |
| BB-DP-5 | 3,961 | 513 | 750 | 7.72 | 5.28 |
| BB-DP-6 | 3,936 | 457 | 661 | 8.61 | 5.95 |
| BB-DP-7 | 2,812 | 411 | 607 | 6.84 | 4.63 |
| BB-DP-8 | 1,265 | 296 | 417 | 4.27 | 3.03 |
| BB-DP-9 | 1,261 | 223 | 327 | 5.65 | 3.86 |
| BB-DP-10 | 7,997 | 825 | 1,210 | 9.69 | 6.61 |
| Mean BB-DP | 4,541 | 512.6 | 748.8 | 8.86 | 6.06 |
| Diabetes Resistant | | | | | |
| BB-DR-1 | 2,750 | 413 | 557 | 6.66 | 4.94 |
| BB-DR-2 | 7,712 | 1,100 | 1,689 | 7.01 | 4.57 |
| BB-DR-3 | 3,574 | 525 | 804 | 6.81 | 4.45 |
| BB-DR-4 | 3,764 | 637 | 967 | 5.91 | 3.89 |
| BB-DR-5 | 2,704 | 541 | 794 | 5.00 | 3.41 |
| BB-DR-6 | 3,392 | 495 | 723 | 6.85 | 4.69 |
| BB-DR-7 | 2,020 | 385 | 539 | 5.25 | 3.75 |
| BB-DR-8 | 3,178 | 274 | 427 | 11.60 | 7.44 |
| BB-DR-9 | 1,968 | 317 | 477 | 6.21 | 4.13 |
| BB-DR-10 | 2,750 | 172 | 270 | 15.99 | 10.19 |
| Mean BB-DR | 3,381 | 485.9 | 724.7 | 8.36 | 5.14 |

TABLE 5

List of bacterial genera whose abundances does not differ statistically at the 1% level of confidence between the diabetes-resistant (BB-DR) and diabetes-prone (BB-DP) stool samples. The percent of total reads is shown for each genus. The percent of reads numbers in bold indicate the genotype (BB-DP or BB-DR), which is higher for that genus. Here a 16S rRNA sequence is considered to be derived from a known genus if the 16S rRNA gene was at a similarity level of 95% or above to its closest cultured relative.

| Approximate genus level - 95% similarity to closest cultured relative | Phyla | % of all BB-DP reads | % of all BB-DR reads | p-value |
|---|---|---|---|---|
| *Rikenella* | Bacteroidetes | 0.002 | 0.022 | 0.025319 |
| *Alistipes* | Bacteroidetes | 1.249 | 1.523 | 0.036159 |
| *Shuttleworthia* | Firmicutes | 0.007 | 0.028 | 0.039739 |
| *Paralactobacillus* | Firmicutes | 0.000 | 0.009 | 0.083698 |
| *Methylobacterium* | Alphaproteobacteria | 0.000 | 0.009 | 0.084358 |
| *Bulleidia* | Firmicutes | 0.000 | 0.009 | 0.087498 |
| *Catonella* | Firmicutes | 0.515 | 0.468 | 0.118618 |
| *Lachnobacterium* | Firmicutes | 0.005 | 0.019 | 0.151877 |
| *Paenibacillus* | Firmicutes | 0.000 | 0.006 | 0.193896 |

TABLE 5-continued

List of bacterial genera whose abundances does not differ statistically at the 1% level of confidence between the diabetes-resistant (BB-DR) and diabetes-prone (BB-DP) stool samples. The percent of total reads is shown for each genus. The percent of reads numbers in bold indicate the genotype (BB-DP or BB-DR), which is higher for that genus. Here a 16S rRNA sequence is considered to be derived from a known genus if the 16S rRNA gene was at a similarity level of 95% or above to its closest cultured relative.

| Approximate genus level - 95% similarity to closest cultured relative | Phyla | % of all BB-DP reads | % of all BB-DR reads | p-value |
|---|---|---|---|---|
| Leptotrichia | Fusobacteria | 0.000 | 0.006 | 0.194076 |
| Hyphomonas | Alphaproteobacteria | 0.000 | 0.006 | 0.194816 |
| Anaerofilum | Firmicutes | 0.000 | 0.006 | 0.194836 |
| Escherichia | Gammaproteobacteria | 0.007 | 0.000 | 0.264014 |
| Papillibacter | Firmicutes | 0.124 | 0.102 | 0.278874 |
| Helicobacter | Epsilonproteobacteria | 0.041 | 0.028 | 0.333493 |
| Porphyromonas | Bacteroidetes | 0.018 | 0.031 | 0.351713 |
| Rothia | Actinobacteria | 0.005 | 0.012 | 0.414772 |
| Anaerotruncus | Firmicutes | 0.005 | 0.012 | 0.417852 |
| Desulfonispora | Firmicutes | 0.000 | 0.003 | 0.439011 |
| Riemerella | Bacteroidetes | 0.000 | 0.003 | 0.439971 |
| Tepidimicrobium | Firmicutes | 0.000 | 0.003 | 0.440071 |
| Acinetobacter | Gammaproteobacteria | 0.000 | 0.003 | 0.441492 |
| Syntrophococcus | Firmicutes | 0.000 | 0.003 | 0.443031 |
| Slackia | Actinobacteria | 0.000 | 0.003 | 0.445231 |
| Parabacteroides | Bacteroidetes | 0.174 | 0.211 | 0.500210 |
| Parvimonas | Firmicutes | 0.005 | 0.000 | 0.504450 |
| Sporotomaculum | Firmicutes | 0.005 | 0.000 | 0.507070 |
| Anaeroplasma | Mollicutes | 0.005 | 0.000 | 0.507710 |
| Dysgonomonas | Bacteroidetes | 0.352 | 0.409 | 0.510250 |
| Thermobrachium | Firmicutes | 0.005 | 0.000 | 0.510950 |
| Acetitomaculum | Firmicutes | 0.011 | 0.019 | 0.553909 |
| Desulfotomaculum | Firmicutes | 0.076 | 0.068 | 0.587288 |
| Peptostreptococcus | Firmicutes | 0.002 | 0.006 | 0.588528 |
| Seinonella | Firmicutes | 0.215 | 0.251 | 0.595608 |
| Acetanaerobacterium | Firmicutes | 0.007 | 0.003 | 0.634067 |
| Hespellia | Firmicutes | 0.048 | 0.062 | 0.635547 |
| Paludibacter | Bacteroidetes | 0.007 | 0.003 | 0.635727 |
| Hallella | Bacteroidetes | 0.009 | 0.006 | 0.698786 |
| Clostridium | Firmicutes | 8.901 | 9.616 | 0.732365 |
| Anaerovorax | Firmicutes | 0.032 | 0.037 | 0.843783 |
| Anaerofustis | Firmicutes | 0.002 | 0.000 | 1 |
| Bacillus | Firmicutes | 0.007 | 0.006 | 1 |
| Corynebacterium | Actinobacteria | 0.002 | 0.000 | 1 |
| Dyella | Gammaproteobacteria | 0.002 | 0.000 | 1 |
| Enterococcus | Firmicutes | 0.002 | 0.003 | 1 |
| Ethanoligenens | Firmicutes | 0.002 | 0.000 | 1 |
| Faecalibacterium | Firmicutes | 0.025 | 0.025 | 1 |
| Gracilibacillus | Firmicutes | 0.005 | 0.003 | 1 |
| Mahella | Firmicutes | 0.002 | 0.000 | 1 |
| Megasphaera | Firmicutes | 0.002 | 0.000 | 1 |
| Oscillatoria | Cyanobacteria | 0.002 | 0.000 | 1 |
| Parasporobacterium | Firmicutes | 0.005 | 0.003 | 1 |
| Rhodothermus | Bacteroidetes | 0.002 | 0.000 | 1 |
| Roseburia | Firmicutes | 0.007 | 0.009 | 1 |
| Sporobacterium | Firmicutes | 0.002 | 0.000 | 1 |
| Tannerella | Bacteroidetes | 0.158 | 0.171 | 1 |
| Total of % reads | | 12.059 | 13.229 | |

TABLE 6

List of bacterial species whose abundance do not differ statistically at the 1% level of confidence between the diabetes-resistant (BB-DR) and diabetes-prone (BB-DP) stool samples. The percent of total reads is shown for each genus. The percent of reads numbers in bold indicate the genotype (BB-DP or BB-DR), which is higher for that genus. Here a 16S rRNA sequence is considered to be derived from a known species if the 16S rRNA gene was at a similarity level of 97% or above to its closest cultured relative.

| Approximate species level - 97% similarity to closest cultured relative | Phyla | % of all BB-DP reads | % of all BB-DR reads | p-value |
|---|---|---|---|---|
| Turicibacter sanguinis | Firmicutes | 0.622 | 0.865 | 0.014120 |
| Bacteroides dorei | Bacteroidetes | 0.245 | 0.382 | 0.015900 |

TABLE 6-continued

List of bacterial species whose abundance do not differ statistically at the 1% level of confidence between the diabetes-resistant (BB-DR) and diabetes-prone (BB-DP) stool samples. The percent of total reads is shown for each genus. The percent of reads numbers in bold indicate the genotype (BB-DP or BB-DR), which is higher for that genus. Here a 16S rRNA sequence is considered to be derived from a known species if the 16S rRNA gene was at a similarity level of 97% or above to its closest cultured relative.

| Approximate species level - 97% similarity to closest cultured relative | Phyla | % of all BB-DP reads | % of all BB-DR reads | p-value |
|---|---|---|---|---|
| Pediococcus claussenii | Firmicutes | 0.016 | 0.000 | 0.016956 |
| Ruminococcus callidus | Firmicutes | 0.085 | 0.047 | 0.017560 |
| Bacteroides intestinalis | Bacteroidetes | 0.101 | 0.180 | 0.022112 |
| Clostridium thermocellum | Firmicutes | 0.126 | 0.084 | 0.025819 |
| Catonella morbi | Firmicutes | 0.002 | 0.021 | 0.027012 |
| Lactobacillus pontis | Firmicutes | 0.650 | 0.611 | 0.044020 |
| Clostridium herbivorans | Firmicutes | 0.016 | 0.047 | 0.050239 |
| Clostridium disporicum | Firmicutes | 1.142 | 1.135 | 0.050478 |
| Parabacteroides distasonis | Bacteroidetes | 0.119 | 0.084 | 0.052619 |
| Pediococcus cellicola | Firmicutes | 0.016 | 0.003 | 0.079058 |
| Ruminococcus schinkii | Firmicutes | 0.055 | 0.031 | 0.081138 |
| Clostridium aerotolerans | Firmicutes | 0.030 | 0.012 | 0.089178 |
| Bulleidia extructa | Firmicutes | 0.000 | 0.009 | 0.092158 |
| Ruminococcus lactaris | Firmicutes | 0.000 | 0.009 | 0.093758 |
| Paralactobacillus selangorensis | Firmicutes | 0.000 | 0.009 | 0.093858 |
| Methylobacterium fujisawaense | Alphaproteobacteria | 0.000 | 0.009 | 0.093918 |
| Clostridium sp. | Firmicutes | 0.025 | 0.009 | 0.105198 |
| Eubacterium minutum | Firmicutes | 0.096 | 0.071 | 0.106438 |
| Clostridium propionicum | Firmicutes | 0.032 | 0.016 | 0.110738 |
| Bacteroides salyersiae | Bacteroidetes | 0.050 | 0.031 | 0.114318 |
| Clostridium clostridioforme | Firmicutes | 0.014 | 0.003 | 0.135697 |
| Ruminococcus luti | Firmicutes | 0.005 | 0.019 | 0.154297 |
| Clostridium quinii | Firmicutes | 0.005 | 0.019 | 0.154897 |
| Clostridium viride | Firmicutes | 0.016 | 0.037 | 0.165717 |
| Lactobacillus kitasatonis | Firmicutes | 0.002 | 0.012 | 0.183456 |
| Clostridium lentocellum | Firmicutes | 0.000 | 0.006 | 0.208096 |
| Hyphomonas polymorpha | Alphaproteobacteria | 0.000 | 0.006 | 0.209956 |
| Lactobacillus sobrius | Firmicutes | 0.011 | 0.003 | 0.234555 |
| Lactobacillus reuteri | Firmicutes | 0.352 | 0.344 | 0.235635 |
| Helicobacter bilis | Epsilonproteobacteria | 0.041 | 0.028 | 0.245095 |
| Sporobacter termitidis | Firmicutes | 0.179 | 0.164 | 0.253875 |
| Lactobacillus kalixensis | Firmicutes | 0.007 | 0.000 | 0.254275 |
| Escherichia albertii | Gammaproteobacteria | 0.007 | 0.000 | 0.256735 |
| Clostridium lituseburense | Firmicutes | 0.023 | 0.040 | 0.301434 |
| Lactococcus garvieae | Firmicutes | 0.037 | 0.059 | 0.313754 |
| Alistipes onderdonkii | Bacteroidetes | 0.002 | 0.009 | 0.335673 |
| Bifidobacterium choerinum | Actinobacteria | 0.002 | 0.009 | 0.336193 |
| Eubacterium eligens | Firmicutes | 0.002 | 0.009 | 0.336733 |
| Clostridium stercorarium | Firmicutes | 0.034 | 0.056 | 0.378412 |
| Rothia nasimurium | Actinobacteria | 0.005 | 0.012 | 0.420092 |
| Anaerotruncus colihominis | Firmicutes | 0.005 | 0.012 | 0.422052 |
| Acinetobacter johnsonii | Gammaproteobacteria | 0.000 | 0.003 | 0.453751 |
| Eubacterium contortum | Firmicutes | 0.000 | 0.003 | 0.454011 |
| Proteiniphilum acetatigenes | Bacteroidetes | 0.000 | 0.003 | 0.454591 |
| Ruminococcus hydrogenotrophicus | Firmicutes | 0.000 | 0.003 | 0.455031 |
| Lactobacillus homohiochii | Firmicutes | 0.000 | 0.003 | 0.455371 |
| Ruminococcus obeum | Firmicutes | 0.000 | 0.003 | 0.455731 |
| Alistipes shahii | Bacteroidetes | 0.000 | 0.003 | 0.455991 |
| Riemerella anatipestifer | Bacteroidetes | 0.000 | 0.003 | 0.456411 |
| Clostridium cylindrosporum | Firmicutes | 0.000 | 0.003 | 0.456711 |
| Streptococcus pseudopneumoniae | Firmicutes | 0.000 | 0.003 | 0.457311 |
| Slackia faecicanis | Actinobacteria | 0.000 | 0.003 | 0.457511 |
| Bifidobacterium animalis | Actinobacteria | 0.007 | 0.016 | 0.479890 |
| Eubacterium desmolans | Firmicutes | 0.007 | 0.016 | 0.484790 |
| Papillibacter cinnamivorans | Firmicutes | 0.005 | 0.000 | 0.499350 |
| Bacteroides plebeius | Bacteroidetes | 0.005 | 0.000 | 0.503410 |
| Clostridium scindens | Firmicutes | 0.146 | 0.186 | 0.529709 |
| Clostridium colinum | Firmicutes | 0.016 | 0.012 | 0.566689 |
| Hespellia porcina | Firmicutes | 0.002 | 0.006 | 0.591848 |
| Peptostreptococcus stomatis | Firmicutes | 0.002 | 0.006 | 0.595288 |
| Alistipes putredinis | Bacteroidetes | 0.675 | 0.800 | 0.604808 |
| Bacteroides eggerthii | Bacteroidetes | 0.039 | 0.053 | 0.610928 |
| Clostridium irregulare | Firmicutes | 0.005 | 0.009 | 0.663227 |
| Streptococcus pneumoniae | Firmicutes | 0.005 | 0.009 | 0.665327 |
| Porphyromonas gingivalis | Bacteroidetes | 0.005 | 0.009 | 0.667327 |
| Lactobacillus vaccinostercus | Firmicutes | 0.009 | 0.006 | 0.695426 |
| Hallella seregens | Bacteroidetes | 0.009 | 0.006 | 0.696046 |
| Bacteroides uniformis | Bacteroidetes | 0.009 | 0.006 | 0.696486 |

TABLE 6-continued

List of bacterial species whose abundance do not differ statistically at the 1% level of confidence between the diabetes-resistant (BB-DR) and diabetes-prone (BB-DP) stool samples. The percent of total reads is shown for each genus. The percent of reads numbers in bold indicate the genotype (BB-DP or BB-DR), which is higher for that genus. Here a 16S rRNA sequence is considered to be derived from a known species if the 16S rRNA gene was at a similarity level of 97% or above to its closest cultured relative.

| Approximate species level - 97% similarity to closest cultured relative | Phyla | % of all BB-DP reads | % of all BB-DR reads | p-value |
|---|---|---|---|---|
| Eubacterium tenue | Firmicutes | 0.007 | 0.012 | 0.707766 |
| Tannerella forsythensis | Bacteroidetes | 0.156 | 0.164 | 0.710786 |
| Bryantella formatexigens | Firmicutes | 0.082 | 0.102 | 0.718446 |
| Clostridium xylanolyticum | Firmicutes | 0.011 | 0.009 | 0.734845 |
| Clostridium amygdalinum | Firmicutes | 0.140 | 0.149 | 0.773805 |
| Clostridium alkalicellum | Firmicutes | 0.034 | 0.034 | 0.845623 |
| Seinonella peptonophila | Firmicutes | 0.215 | 0.251 | 0.881002 |
| Alistipes finegoldii | Bacteroidetes | 0.295 | 0.335 | 1 |
| Clostridium algidixylanolyticum | Firmicutes | 0.002 | 0.000 | 1 |
| Clostridium sporosphaeroides | Firmicutes | 0.005 | 0.006 | 1 |
| Corynebacterium mastitidis | Actinobacteria | 0.002 | 0.000 | 1 |
| Desulfotomaculum guttoideum | Firmicutes | 0.009 | 0.012 | 1 |
| Dyella japonica | Gammaproteobacteria | 0.002 | 0.000 | 1 |
| Enterococcus dispar | Firmicutes | 0.002 | 0.003 | 1 |
| Eubacterium ruminantium | Firmicutes | 0.002 | 0.000 | 1 |
| Gracilibacillus orientalis | Firmicutes | 0.005 | 0.003 | 1 |
| Hespellia stercorisuis | Firmicutes | 0.002 | 0.003 | 1 |
| Lactobacillus acidophilus | Firmicutes | 0.007 | 0.009 | 1 |
| Lactobacillus catenaformis | Firmicutes | 0.002 | 0.000 | 1 |
| Lactobacillus gastricus | Firmicutes | 0.002 | 0.000 | 1 |
| Lactobacillus jensenii | Firmicutes | 0.002 | 0.000 | 1 |
| Lactobacillus plantarum | Firmicutes | 0.002 | 0.000 | 1 |
| Lactobacillus vaginalis | Firmicutes | 0.005 | 0.003 | 1 |
| Mahella australiensis | Firmicutes | 0.002 | 0.000 | 1 |
| Paludibacter propionicigenes | Bacteroidetes | 0.005 | 0.003 | 1 |
| Prevotella baroniae | Bacteroidetes | 0.002 | 0.000 | 1 |
| Prevotella bryantii | Bacteroidetes | 0.005 | 0.003 | 1 |
| Rhodothermus marinus | Bacteroidetes | 0.002 | 0.000 | 1 |
| Roseburia intestinalis | Firmicutes | 0.002 | 0.000 | 1 |
| Shuttleworthia satelles | Firmicutes | 0.002 | 0.000 | 1 |
| Total of % reads | | 6.135 | 6.796 | |

Example 7—Determination of *Lactobacillus* Dosage in Bb-DP Rats

An overly permeable gut has been found in BB rats and humans with type 1 diabetes. This physiological environment results in the translocation of normal flora or its metabolites to other organs. Considering this information was particularly relevant to determine the appropriate dosage of microorganisms for feeding experiments. The dosage of *Lactobacillus* can range from $10^9$ cells/animal for a mixed culture of *Lactobacillus* species to as low as $10^4$/animal for a pure culture of *L. reuteri*.

To determine the dosage of *Lactobacillus* strains capable of delaying or inhibiting the onset of type 1 diabetes, *Lactobacillus* strains isolated from diabetes-resistant rats (BB-DR) were administered to diabetes-prone rats (BB-DP). Briefly, a pilot experiment was performed by feeding *L. johnsonii* N6.2 or *L. reuteri* TD1 (strains isolated from BB-DR rats) to 1-day-old BB-DP rats during mother feeding for seven days to establish the optimal dosage of bacteria that can be administered to BB-DP rats without deleterious effects. The two lactic acid bacterial strains were administered individually ($1\times10^6$ or $1\times10^8$ per animal per day) by oral gavage to 1-day-old BB-DP rats (N=5) during mother feeding for seven days. Colonies with different morphologies were isolated from either Rogosa (*Lactobacillus* selective media 14) or BHI plates (for anaerobes).

Figure 6:
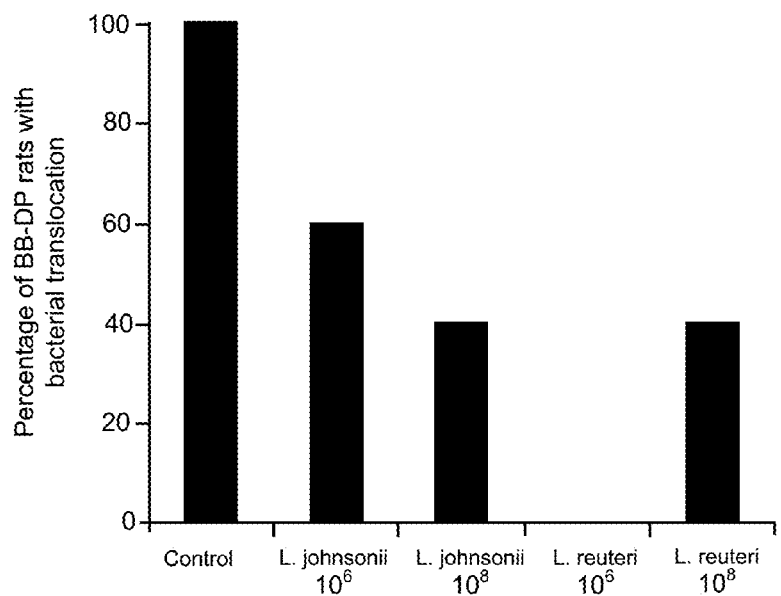
FIG. 6 shows percentage of BioBreeding diabetes-prone (Biomedical Research Models, Worcester, Mass.; BB-DP; N=5 per group) rats that exhibited bacterial translocation to the spleen and pancreas on Blood BHI plates. BB-DP pups were administered with *L. johnsonii* N6.2 or *L. reuteri* TD1 at $10^6$ or $10^8$ CFU/animal. Same results were observed on MRS agar.

The results, as shown in FIG. 6, demonstrate that the administration of *Lactobacillus* prevents or significantly reduces bacteria translocation. In the control group (PBS fed), 60% of the animals had culturable bacteria in the spleen and liver (FIG. 6). The sequencing of the 16S RNA gene showed that different bacterial genera translocated to the spleen and liver in the control group. The genera found were: *Paenibacillus, Bacillus, Escherichia, Lactococcus*, and *Lactobacillus*. These data revealed that BB-DP rats exhibit greater intestinal permeability.

In comparison, no translocation was observed in rats fed with $1\times10^6$ *L. reuteri* TD1. In addition, only 20% translocation was observed in rats fed with *L. reuteri* TD1 at higher dosage ($1\times10^8$). This not only revealed that *L. reuteri* can be administered at either dose to the BB-DP rats, but more importantly, that the administration of *L. reuteri* TD1 can prevent bacterial translocation. A similar level of translocation was observed in rats fed with *L. johnsonii* N6.2 regardless of dose, albeit a lower level of bacteria translocation was observed in the control group.

Further, within the *Lactobacillus* fed groups, colonies isolated from the animals that showed bacterial translocation followed a similar distribution as found in the control group. This finding reveals that the feeding had a general protective effect rather than the targeted inhibition of a specific genus of bacteria.

Example 8—Decreased Incidence of Diabetes in Bb-Dp Rats Fed with *L. Johnsonhii* 6.2

To determine the ability of *Lactobacillus* strains for delaying or inhibiting the onset of type 1 diabetes, *Lacto-*

*bacillus* strains isolated from diabetes-resistant rats (BB-DR) were administered to diabetes-prone rats (BB-DP).

Figure 7:
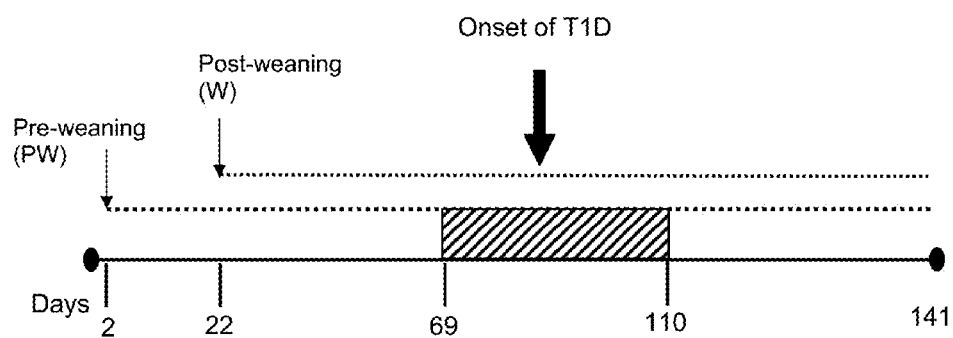
FIG. 7 shows the feeding design using BB-DP animals. Bacterial strains were administered to BB-DP rats to test whether they would delay or inhibit the onset of type 1 diabetes. *L. reuteri* TD1 or *L. johnsonii* N6.2 suspensions ($10^8$ CFU) were administered daily by oral gavage. All experiments were conducted with Institutional Animal Care and adherence to prescribed IACUC protocol. Starting on Day 60, the blood glucose levels of animals were taken weekly using a glucose monitor (Accu-chek, Roche Diagnostics). If glucose levels surpassed 250 mg/dl for two consecutive days, the rat was considered diabetic. Immediately after disease development the rat was sacrificed. Organs and tissues were harvested and preserved for analysis as described in Neu et al. (2005), which is hereby incorporated by reference in its entirety. Arrow in black indicates the time that feeding was started. The dashed line indicates daily feeding. The dashed box indicates the period in which rats developed diabetes.
Figure 8A:
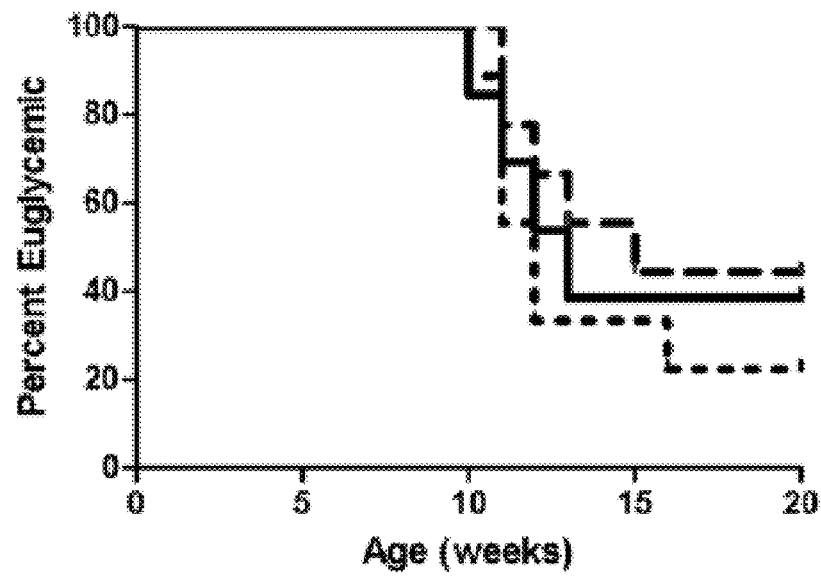
FIGS. 8A-8B show Kaplan-Meier plot depicting the survival of BB-DP rats feed 8A) pre-weaning or 8B) post-weaning with *L. johnsonii* N6.2 (short dashed line), or *L. reuteri* TD1 (long dashed line) compared to the PBS feed control (solid line) (N=10 per group).
Figure 8B:
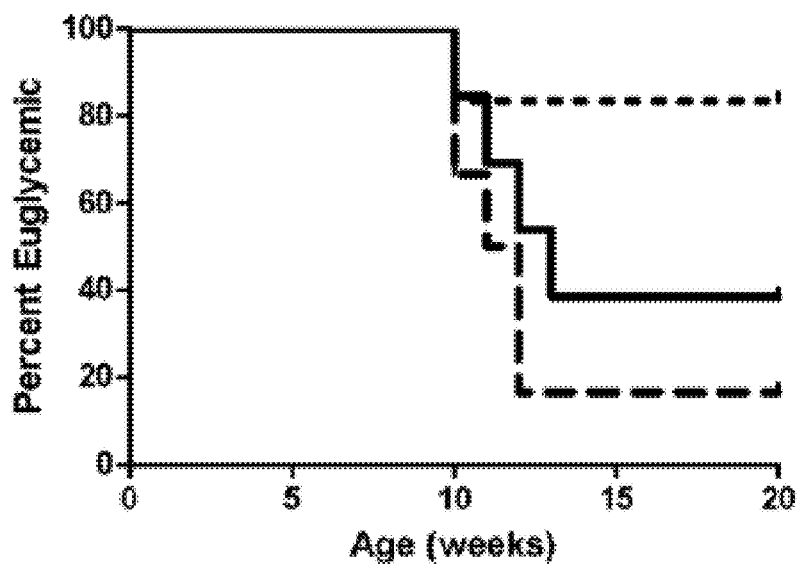

Briefly, *L. reuteri* TD1 or *L. johnsonii* N6.2 suspensions ($1 \times 10^8$ CFU per animal) were administered i) pre-weaning to 1-day-old BB-DP rats during mother feeding; and ii) post-weaning to 21-day-old BB-DP rats (FIG. 7). The results, as shown in FIGS. 8A-8B, demonstrated that post-weaning administration of *L. johnsonii* N6.2 can delay the onset of diabetes in a rat model for up to 20 weeks. The post-weaning administration of *L. johnsonii* N6.2 produced the most significant beneficial effects on decreasing the incidence of diabetes (FIG. 8, P<0.04).

Example 9—Administration of *L. Johnsonii* N6.2. Modifies the Intestine Microbiota The impact of *L. johnsonii* N6.2. feeding on the intestinal microbiota was determined. RT-qPCR experiments were performed to measure the concentration of *Pseudomonas, Bacteroides, Staphylococcus, Bifidobacterium, Clostridium, Lactobacillus*, and enterobacteria in either the ileac or colonic content. Main groups of microorganisms were cultured as the animals developed diabetes. The abundance of specific bacterial genera was also measured by RT-qPCR.

Figure 9A:
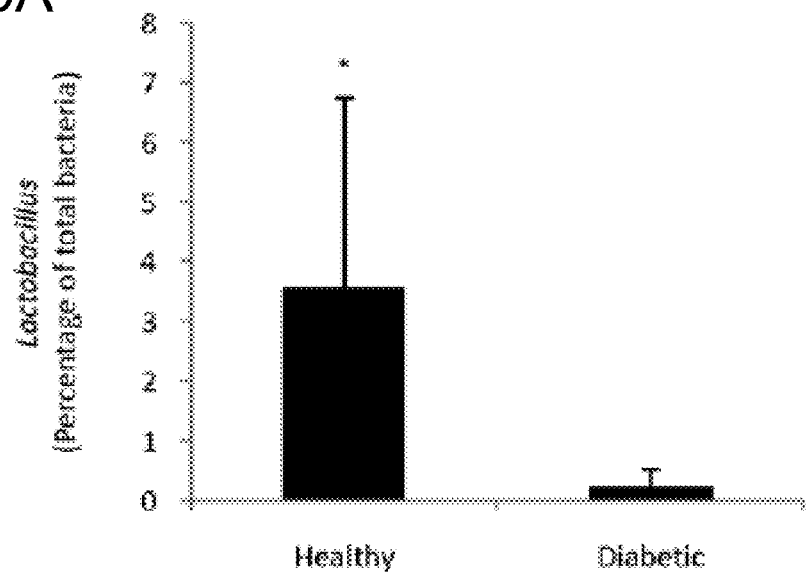
FIGS. 9A-9B show quantification using real time qPCR of lactobacilli (9A) and enterobacteria (9B) from Ileal mucosa. The values are expressed as mean of the percentages from total bacteria determined from 5 ng of DNA. * indicates significant differences (P<0.05) between healthy and diabetic animals (N=6 per group).
Figure 9B:
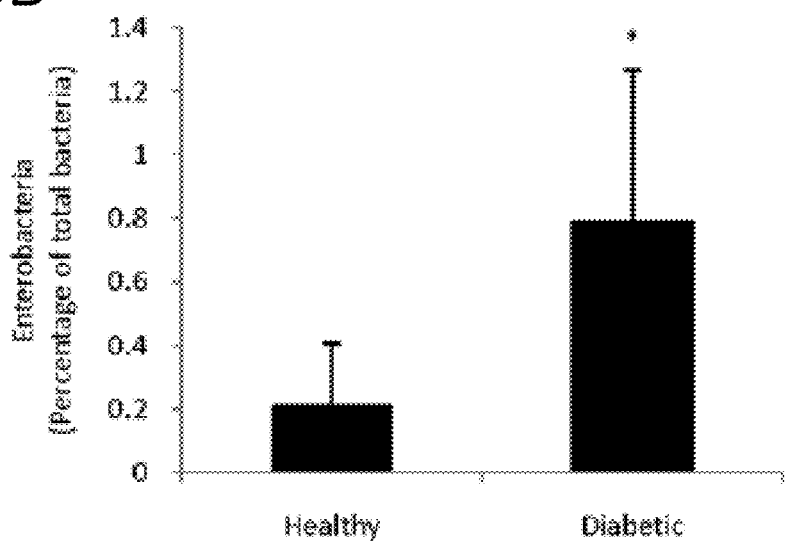

Analysis of the ileac mucosa, as shown in FIGS. 9A-9B, unveiled an increase in the *Lactobacillus* population in the healthy rats; while a higher concentration of enterobacteria were found in the diabetic rats (FIG. 9). In addition, no statistically significant differences were observed on the stool culturable bacterial fractions of *Lactobacillus, Bacteroides*, or in the total anaerobe counts. The lack of differences of the microbiota in the stool samples, coupled with the statistically significant differences of microbiota in the ileal mucosa, demonstrate that the administration of *L. johnsonii* N6.2 could decrease the passage of pro-inflammatory antigens into the intestinal mucosa.

Example 10—The Gene Expression of Tight Junction Proteins is Modified Upon *L. Johnsonii* Administration It has been found that before the onset of diabetes, BB rats exhibit lower levels of the major intercellular tight junction protein claudin-1 and greater intestinal permeability. The early increment in intestinal permeability in the BB-DP rats allow unregulated passage of environmental antigens, which could trigger autoimmune responses leading to type 1 diabetes.

To determine the effect of *L. johnsonii* N6.2 on intestinal integrity, macroscopic modifications in the mucosal architecture were examined on hematoxylin and eosin stained slides of distal small intestine.

Figure 10A:
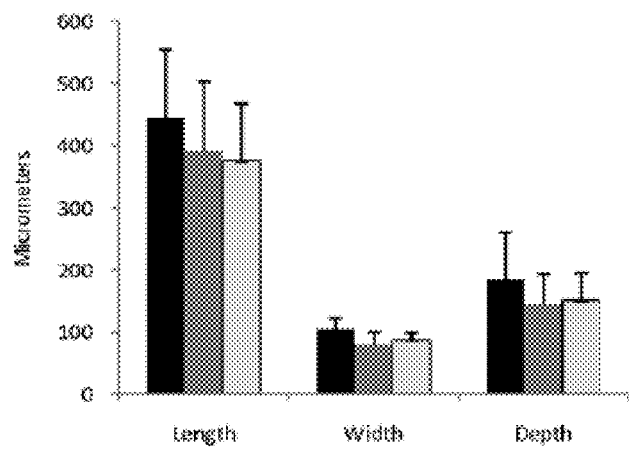
FIGS. 10A-10C show effect of the post weaning administration of *L. johnsonii* on the intestinal morphology (10A, 10B) and on mRNA levels of tight junction genes (10C). Hematoxylin and eosin stained slides of distal small intestine were examined for morphological changes. (10A) shows measurements of crypt depth, villus height and villus width in *L. johnsonii* fed group (black bars), healthy control (dark grey bars) and diabetic group (light grey bars). (10B) shows percentage of goblet cells in the distal small intestine in the different treatment groups. (10C) shows RT-qPCR analysis of the expression of tight junction genes. Relative amounts of claudin-1 and occludin were calculated by subtracting the internal control (β actin) and changes in expression levels were calculated relative to its value in the *L. johnsonii* fed group (expression=1). Grey bars: Relative expression in the healthy control; Black bars: relative expression in the diabetic animals. The values are means+ S.D. (N=10); * P<0.05; **P<0.0001; #P<0.01.
Figure 10B:
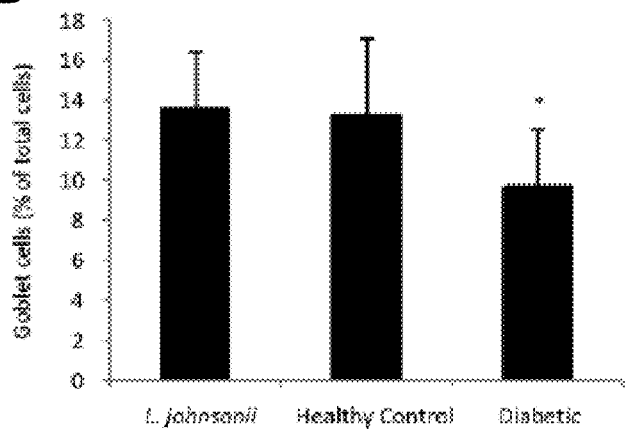
Figure 10C:
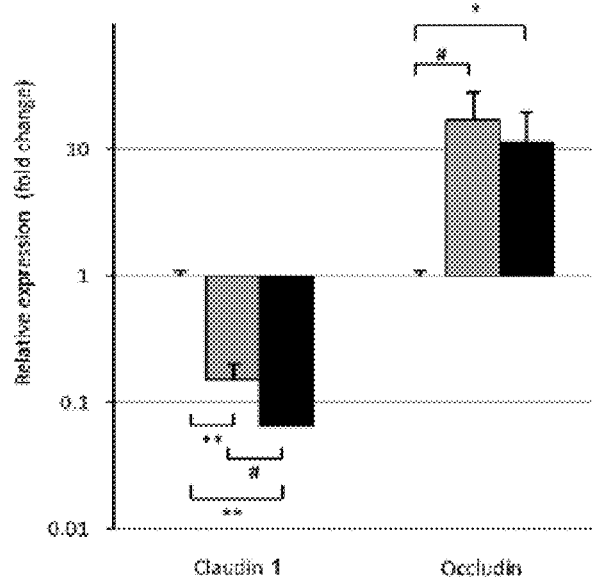

The results, as shown in FIGS. 10A-10C, revealed that no morphological differences between the *L. johnsonii* fed group, control healthy, or diabetic animals were found in villus height or width or crypt depth (FIG. 10A). In addition, necrosis was not observed. Compared to diabetic animals, healthy animals had a significantly higher amount of goblet cells (FIG. 10B, p<0.05).

At the molecular level, the expression level of claudin-1 and occludin proteins involved in tight junction assembly and maintenance were also measured. The results showed that the feeding of *L. johnsonii* upregulated the expression of claudin-1 and decreased the expression of occludin. The beneficial effects of *L. johnsonii* could be due to an amelioration of the barrier dysfunction observed in this animal model. Specifically, BB-DP rats exhibited low levels of the sealing claudin-1 but high levels of occludin TJ-related transmembrane protein (FIG. 10C).

Example 11—Effects of *L. Johnsonii* on Host Oxidative Stress Response

Reactive oxygen species (ROS) species are generated early during disease development. These ROS species negatively affect the normal function of tissue and organs in various ways, including the disruption of epithelial tight junctions, leading to malfunction and tissue necrosis.

The host response to oxidative stress is complex. Multiple pathways of detoxification of reactive oxygen species (ROS) are involved in response to oxidative stress, including superoxide dismutase 1 and 2 (Sod1, Sod2), catalase (Cat), glutathione reductase (GR), and glutathione peroxidase (Gpx1) pathways.

The levels of hexanoyl-lysine, which is a biomarker for oxidative stress, have been determined by ELISA on ileum mucosa and were variable among the animals tested. It has been found that hexanoyl-lysine levels were significantly higher (P<0.05) in diabetic animals (53±21 µM·min−1) when compared to healthy animals (14±10 µM·min−1).

Figure 11A:
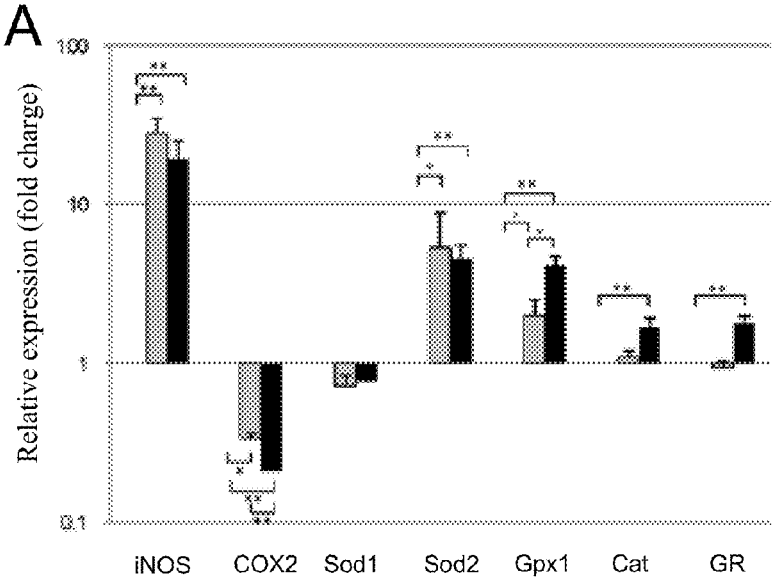
FIGS. 11A-11B show assessment of the oxidative stress response in the host. (11A) shows RT-qPCR analysis of the expression of genes linked to the oxidative stress response in the host. Relative amounts of iNOS, Cox2, Sod1, Sod2, Gpx1, Cat, and GR were calculated by subtracting the internal control (β actin), and changes in expression levels were calculated relative to the value in *L. johnsonii*-fed group (expression=1). Grey bars: relative expression in the healthy control; Black bars: relative expression in the diabetic animals. The values are means+S.D. (N=6); *P<0.05; ° P<0.01, **P<0.0001. (11B) shows western blot analysis of iNOS levels. β actin was used as internal control.

To further determine specific mechanisms involved, the mRNA levels of different enzymes involved in ROS detoxification pathways were measured. The results, as shown in FIG. 11A, revealed that all of the genes measured, except Sod1, were induced in the diabetic animals (FIG. 11A); whereas Sod1 expression was not modified under any condition.

Figure 11B:
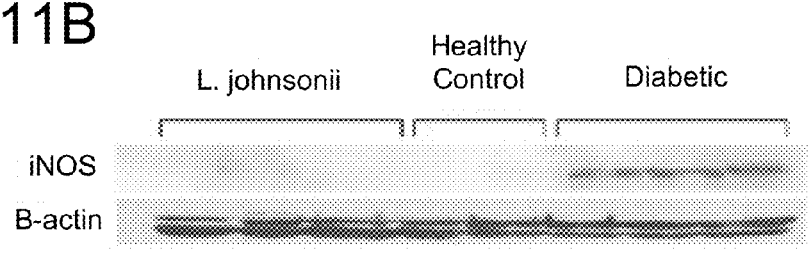

Specifically, the expression of Sod2 and Gpx1 was induced in the diabetic animals (~4.5 folds and ~4 folds, respectively; P<0.05) and to a lesser extent Cat and GR (~2 and 1.8 folds, respectively). By comparing the mRNA levels within the healthy animals (healthy controls vs. *L. johnsonii* fed group), it is determined that Cat and GR induction is correlated with the diabetic status of the animal. Gpx1 showed a higher response in the *L. johnsonii* fed group compared to healthy controls; while Sod2 was repressed only in the *L. johnsonii* fed group. In addition, the expression of Cox2 was repressed in diabetic animals (FIG. 11A, P<0.001), as compared to the *L. johnsonii* fed group.ROS also leads to the synthesis of nitric oxide by inducing nitric oxide synthase (iNOS). Nitric Oxide is a signaling molecule involved in the immune response against pathogens as well as early stages of many autoimmune diseases. The results, as shown in FIG. 11A, revealed that the mRNA levels of iNOS were significantly repressed in the *L. johnsonii* fed group, when compared to diabetic animals (~22 fold, FIG. 11A, P<0.0001). Although no differences were observed between the control groups (healthy and diabetic), western blot analysis showed that iNOS expression is reduced in fed and control healthy groups (FIG. 11B), indicating that low levels of iNOS are correlated with the healthy status of the animals.

Example 12—Effects of *L. Johnsonii* on Tnfα and Ifnγ Expression iNOS modulates transcription and catalytic activity of cyclooxygenase 2 (Cox-2), which is directly linked to the prostaglandin production pathway. It is determined that mRNA levels of Cox2 were repressed 4 folds in diabetic BB rats. Similar repressive effect was observed in the levels of prostaglandin D synthase; while such repressive effect was reverted when insulin was administered. In addition, IFNγ, an important mediator of inflammatory responses with pleiotropic effects in the host, induces the expression of iNOS while represses the expression of Cox2.

Figure 12:
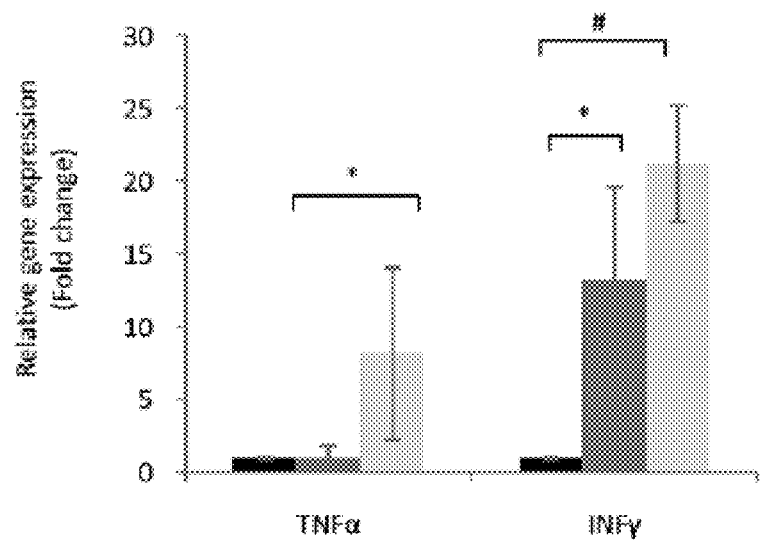
FIG. 12 shows mRNA levels of the pro-inflammatory cytokine genes, IFNγ and TNFα linked to the oxidative stress response in the host. Relative expression was calculated as previously described relative to the value in the *L. johnsonii*-fed group (expression=1). Relative expression in the *L. johnsonii*-fed group (black bars); healthy control (dark grey bars) and diabetic animals (light grey bars). The values are means+S.D. (N=6); *P<0.05; #P=0.01.

Thus, this Example examined whether there is a negative correlation between the levels of various molecules, including IFNγ and other pro-inflammatory cytokines like TNFα, and *L. johnsonii*-mediated decrease in oxidative stress response in the host. The results, as shown in FIG. 12, revealed that mRNA levels of TNFα differ in ~7 folds (P<0.05) between the healthy and diabetic animals; however, no differences in TNFα were observed within the healthy animals (FIG. 12). The results indicate that the modification in TNFα is correlated with the healthy status and not with the administration of the probiotic bacteria.

The expression of IFNγ, on the contrary, was related to the administration of *L. johnsonii* N6.2. In the diabetic animals, a ~20-fold higher expression (P<0.005) of IFNγ was observed, as compared to the *L. johnsonii* N6.2 fed group. The lack of significant differences between the healthy controls and diabetic animals indicated that probiotic microorganisms contribute to the decrement of the inflammatory responses.

Example 13—The Effect of *L. Johnsonii* on Indoleamine 2,3-Dioxygenase Expression (IDO)

Indoleamine 2,3-Dioxygenase expression (IDO) is an enzyme expressed at high levels in the small intestine and has been implicated in the regulation of intestinal inflammation. In NOD mice, IDO is a protective regulator of autoimmune responses. IDO mRNA levels in ileal mucosa follow a similar pattern of expression as shown for IFNγ (FIG. 12), a known inducer of IDO.

Figure 13:
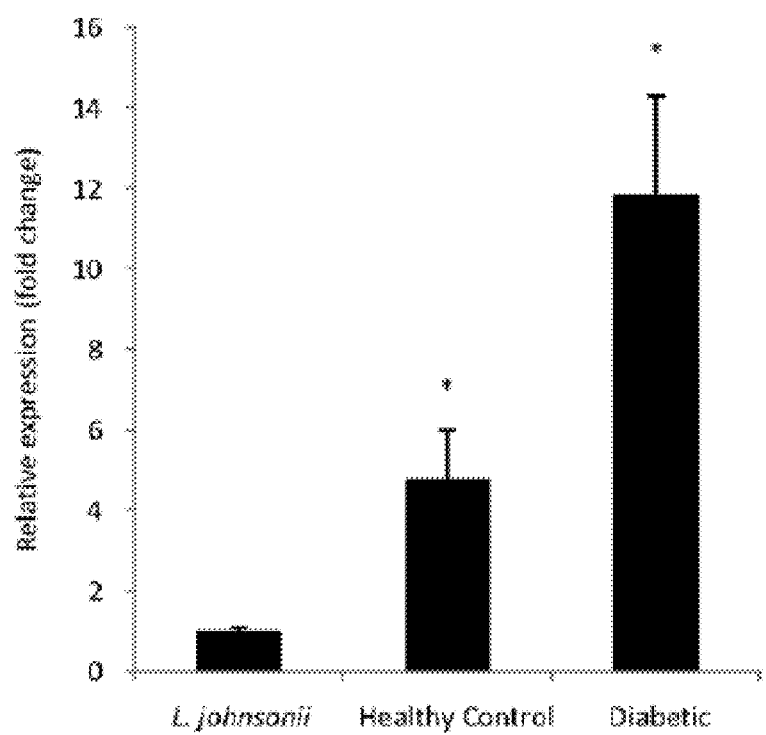
FIG. 13 shows mRNA levels of IDO ileac mucosa. Relative expression was calculated based on mRNA levels of each group relative to the mRNA level in the *L. johnsonii* fed group (expression=1). The values are means+S.D. (N=6); *P<0.05.

As shown in FIG. 13, *L. johnsonii* N6.2 fed animals had a 12-fold higher level of IDO expression, as compared to diabetic animals (FIG. 13); while a 4-fold lower expression in healthy animals was observed. These data revealed that IDO could act as a down regulator of the B cell homeostatic responses to commensal microbiota.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

Altschul S, Madden T, Schaeffer A, Zhang J, Zhang Z, Miller W, Lipman, D. (1997) Gapped BLAST and PSI-BLAST: a new generation of protein database search programs. *Nucleic Acids Res* 25: 3389-3402.

Arumugam T V, Arnold N, Proctor L M, Newman M, Reid R C, Hansford K A, Fairlie D P, Shiels I A, Taylor S M: Comparative protection against rat intestinal reperfusion injury by a new inhibitor of sPLA2, COX-1 and COX-2 selective inhibitors, and an LTC4 receptor antagonist. *Br J Pharmacol* 140:71-80, 2003

Bernet-Camard M F, Lie'vin V, Brassart D, Neeser J R, Servin A L, Hudault S. (1997) The human *Lactobacillus acidophilus* strain LA1 secretes a nonbacteriocin antibacterial substance(s) active in vitro and in vivo. *Appl Environ Microbiol* 63: 2747-2753.

Biavati B, Mattarelli, P, Crociani F. (1991) *Bifidobacterium saeculare*: a new species isolated from faeces of rabbit. System. *Appl Microbiol* 14: 389-392.

Bosshard P P, Stettler R, Bachofen R (2000) Seasonal and spatial community dynamics in the meromictic Lake Cadagno. *Arch Microbiol* 174: 168-174.

Brugman S, Klatter F A, Visser J T J, Wildeboer-Veloo A C M, Harmsen H J M, Rozing J, Bos N A. (2006) Antibiotic treatment partially protects against type 1 diabetes in the Bio-Breeding diabetes-prone rat. Is the gut flora involved in the development of type 1 diabetes? *Diabetologia* 49: 2105-2108.

Byun, R, Nadkarni, M A, Chhour K L, Martin, F E, Jacques N A, Hunter N. (2004) Quantitative analysis of diverse *Lactobacillus* species present in advanced dental caries. *J Clin Microbiol* 42: 3128-36.

Calcinaro F, Dionisi S, Marinaro M, Candeloro P, Bonato V, Marzotti S, Cornell R B, Ferretti E, Gulino A, Grasso F, De Simone C, Di Mario U, Falorni A, Boirivant M, Dotta F. (2005) Oral probiotic administration induces interleukin-10 production and prevents spontaneous autoimmune diabetes in the non-obese diabetic mouse. *Diabetologia* 48: 1565-1575.

Čepeljnik T, Lah, B, Narat M, Marinšek-Logar R. (2007) Adaptation of adhesion test using caco-2 cells for anaerobic bacterium *Pseudobutyrivibrio xylanivorans*, a probiotic candidate. *Folia Microbiol (Praha)* 52: 367-373.

Čepeljnik T, Zorec M, Kostanjsek R, Nekrep F V, Marinsek-Logar R. (2003) Is *Pseudobutyrivibrio xylanivoransstrain* Mz5T suitable as a probiotic? An in vitro study. *Folia Microbiol (Praha)* 48: 339-45.

Delroisse J M, Boulvin A L, Parmentier I, Dauphin R D, Vandenbol M, Portetelle D (2008) Quantification of *Bifidobacterium* spp. and *Lactobacillus* spp. in rat fecal samples by real-time PCR. *Microbiol Res* 163: 663-670.

DeSantis, T. Z., P. Hugenholtz, K. Keller, E. L. Brodie, N. Larsen, Y. M. Piceno, R. Phan, and G. L. Andersen. 2006. NAST: a multiple sequence alignment server for comparative analysis of 16S rRNA genes. *Nucleic Acids Res* 34:W394-9.

Edgar R C. (2004) MUSCLE: multiple sequence alignment with high accuracy and high throughput. *Nucleic Acids Res* 32: 1792-1797.

Elder M E, Maclaren N. (1983) Identification of profound peripheral T lymphocyte immunodeficiencies in the spontaneously diabetic BB rat. *J Immunol* 130:1723-1731.

Fisher M M, Triplett E W (1999) Automated approach for ribosomal intergenic spacer analysis of microbial diversity and its application to freshwater bacterial communities. *Appl Environ Microbiol* 65: 4630-4636.

Fukuda S, Suzuki Y, Murai M, Asanuma N, Hino T. (2006) Isolation of a novel strain of *Butyrivibrio fibrisolvens* that isomerizes linoleic acid to conjugated linoleic acid without hydrogenation, and its utilization as a probiotic for animals. *J Appl Microbiol* 100: 787-794.

Greiner D L, Rossin A A, Mordes J P. (2001) Translating data from animal models into methods for preventing human autoimmune diabetes mellitus: *caveat emptor and primum non nocere*. *Clin Immunol* 100: 134-143.

Gye M C: Changes in the expression of claudins and transepithelial electrical resistance of mouse Sertoli cells by Leydig cell coculture. *Int J Androl* 26:271-8, 2003

Hamady M, Walker J, Harris J K, Gold N J, Knight R. (2008) Error-correcting barcoded primers for pyrosequencing hundreds of samples in multiplex. *Nature Methods* 5: 235-237.

Hooper L V. (2004) Bacterial contributions to mammalian gut development. *Trends Microbiol* 12: 129-134.

Hooper L V, Gordon J I. (2001) Commensal host-bacterial relationships in the gut. *Science* 292: 1115-1118.

Huang X, Wang J, Alum S, Yang S P, Hillier L. (2003) PCAP: a whole-genome assembly program. *Genome Res* 13: 2164-2170.

Hughes J B, Hellmann J J, Ricketts T H, Bohannan B J M. (2001) Counting the uncountable: statistical approaches to estimating microbial diversity. *Appl Environ Microbiol* 67: 4399-4406.

Iwakoshi N N, Greiner D L, Rossini A A, Mordes J P. (1999) Diabetes prone BB rats are severely deficient in natural killer T cells. *Autoimmunity* 31:1-14.

Jack R W, Tagg J R, Ray B. (1995) Bacteriocins from Gram-positive bacteria. *Microbiol Rev* 59: 171-200.

Kim J F, Jeong H, Yu D S, Choi S H, Hur C G, Park M S, Yoon S H, Kim D W, Ji G E, Park H S, Oh T K. 2008. Genome sequence of the probiotic bacterium *Bifidobacterium animalis* subsp. *lactis* AD011. *J Bacteriol*. November 14. [Epub ahead of print]

Klaenhammer T, Altermann E, Arigoni F, Bolotin A, Breidt F, Broadbent J, Cano R, Chaillou S, Deutscher J, Gasson M, van de Guchte M, Guzzo J, Hartke A, Hawkins T, Hols P, Hutkins R, Kleerebezem M, Kok J, Kuipers O, Lubbers M, Maguin E, McKay L, Mills D, Nauta A, Overbeek R, Pel H, Pridmore D, Saier M, van Sinderen D, Sorokin A, Steele J, O'Sullivan D, de Vos W, Weimer B, Zagorec M, Siezen R. (2002) Discovering lactic acid bacteria by genomics. *Antonie Van Leeuwenhoek* 82: 29-58.

Leahy S C, Higgins D G, Fitzgerald G F, van Sinderen D. (2005) Getting better with bifidobacteria. *J Appl Microbiol*. 98: 1303-1315.

Lee J H, Karamychev V N, Kozyavkin S A, Mills D, Pavlov A R, Pavlova N V, Polouchine N N, Richardson P M, Shakhova V V, Slesarev A I, Weimer B, O'Sullivan D J. (2008) Comparative genomic analysis of the gut bacterium *Bifidobacterium longum* reveals loci susceptible to deletion during pure culture growth. *BMC Genomics*. 9: 247.

Li W, Godzik A. (2006) Cd-hit: a fast program for clustering and comparing large sets of protein or nucleotide sequences. *Bioinformatics* 22: 1658-1659.

Like A A, Guberski D L, Butler L. (1991) Influence of environmental viral agents on frequency and tempo of diabetes-mellitus in BB/WOR rats. *Diabetes* 40: 259-262.

Lorca G L, Wadstrom T, de Valdez G F, Ljungh A. (2001) *Lactobacillus acidophilus* autolysins inhibit *Helicobacter pylori* in vitro, *Curt Microbiol* 42: 39-44.

Lozupone C, Hamady M, Knight R. (2006) UniFrac—an online tool for comparing microbial community diversity in a phylogenetic context. *BMC Bioinformatics* 7: 371.

Makarova K, Slesarev A, Wolf Y, Sorokin A, Mirkin B, Koonin E, Pavlov A, Pavlova N, Karamychev V, Polouchine N, Shakhova V, Grigoriev I, Lou Y, Rohksar D, Lucas S, Huang K, Goodstein D M, Hawkins T, Plengvidhya V, Welker D, Hughes J, Goh Y, Benson A, Baldwin K, Lee J H, Diaz-Muñiz I, Dosti B, Smeianov V, Wechter W, Barabote R, Lorca G, Altermann E, Barrangou R, Ganesan B, Xie Y, Rawsthorne H, Tamir D, Parker C, Breidt F, Broadbent J, Hutkins R, O'Sullivan D, Steele J, Unlu G, Saier M, Klaenhammer T, Richardson P, Kozyavkin S, Weimer B, Mills D. (2006) Comparative genomics of the lactic acid bacteria. *Proc Natl Acad Sci USA* 103: 15611-15616.

Mai V, Colbert L H, Perkins S N, Schatzkin A, Hursting S D. (2007) Intestinal microbiota: a potential diet-responsive prevention target in Apc$^{Min}$ mice. *Molecular Carcinogenesis* 46: 42-48.

Martin B, Jofré A, Garriga M, Pla M, Aymerich T. (2006) Rapid quantitative detection of *Lactobacillus sakei* in meat and fermented sausages by real-time PCR. *Appl Environ Microbiol*. 72: 6040-6048.

Matsuda K, Tsuji H, Asahara T, Kado Y, Nomoto K: Sensitive quantitative detection of commensal bacteria by rRNA-targeted reverse transcription-PCR. *Appl Environ Microbiol* 73:32-39, 2007

Matsuzaki T, Nagata Y, Kado S, Uchida K, Kato I, Hashimoto S, Yokokura T. (1997) Prevention of onset in an insulin-dependent diabetes mellitus model, NOD mice, by oral feeding of *Lactobacillus casei*. *APMIS* 105: 643-649.

Mazmanian S K, Liu C H, Tzianabos A O, Kasper D L. (2005) An immunomodulatory molecule of symbiotic bacteria directs maturation of the host immune system. *Cell* 122: 107-118.

McInerney M F, Pek S B, Thomas D W (1991) Prevention of insulitis and diabetes onset by treatment with complete Freund's adjuvant in NOD mice. *Diabetes* 40:715-725.

Mordes J P, Bortell R, Blankenhorn E P, Rossini A A, Greiner D L. (2004) Rat models of type 1 diabetes: genetics, environment, and autoimmunity. *ILAR Journal* 45: 278-291.

Neu J, Reverte C M, Mackey A D, Liboni K, Tuhacek-Tenace L M, Hatch M, Li N, Caicedo R A, Schatz D A, Atkinson M. (2005) Changes in intestinal morphology and permeability in the biobreeding rat before the onset of type 1 diabetes. *J Pediatr Gastroenterol Nutr* 40:589-95.

Neumann H, Schmidt H, Wilharm E, Behrens L, Wekerle H. Interferon gamma gene expression in sensory neurons: evidence for autocrine gene regulation. *J Exp Med* 186: 2023-31, 1997

Ohkawara S, Furuya H, Nagashima K, Asanuma N, Hino T. (2006) Effect of oral administration of *Butyrivibrio fibrisolvens* MDT-1 on experimental enterocolitis in mice. *Clin Vaccine Immunol* 13: 1231-1236.

Ohkawara S, Furuya H, Nagashima K, Asanuma N, Hino T. (2005) Oral administration of *Butyrivibrio fibrisolvens*, a butyrate-producing bacterium, decreases the formation of aberrant crypt foci in the colon and rectum of mice. *J Nutr* 135: 2878-2883.

Ranjard L, Poly L F, Lata J C, Mougel C, Thioulouse J, Nazaret S. (2001) Characterization of bacterial and fungal soil communities by automated ribosomal intergenic spacer analysis fingerprints: Biological and methodological variability. *Appl Env Microbiol* 67: 4479-4487.

Reid G, Joss J, Sebulsky M T, McCormick J K. (2003) Potential uses of probiotics in clinical practice. *Clin Microbiol Rev* 4: 658-672.

Roesch, L F W, Fulthorpe R R, Riva A, Casella G, Hadwin A K M, Kent A D, Daroub S, Camargo F A O, Farmerie W G, Triplett E W (2007) Pyrosequencing enumerates and contrasts soil microbial diversity. *ISME J* 1: 283-290.

Roesch L F, Lorca G L, Casella G, Giongo A, Naranjo A, Pionzio A M, Li N, Mai V, Wasserfall C H, Schatz D, Atkinson M A, Neu J, Triplett E W: Culture-independent identification of gut bacteria correlated with the onset of diabetes in a rat model. *ISME J* 5:536-48, 2009

Sadelain M W J, Qin H Y, Lauzon J, Singh B. 1990a. Prevention of type-1 diabetes in NOD mice by adjuvant immunotherapy. *Diabetes* 39:583-589.

Sadelain M W J, Qin H Y, Sumoski W, Parfeny N, Singh B, Rabinovitch A. 1990b. Prevention of diabetes in the BB rat by early immunotherapy using Freund adjuvant. *J Autoimmunity* 3:671-680.

Salminen S, Benno Y, de Vos W. (2006) Intestinal colonisation, microbiota and future probiotics? *Asia Pac J Clin Nutr* 15: 558-562.

Schell, M A, Karmirantzou M, Snel B, Vilanova D, Berger B, Pessi G, Zwahlen M C, Desiere F, Bork P, Delley M, Pridmore R D, Arigoni F. (2002) The genome sequence of *Bifidobacterium longum* reflects its adaptation to the human gastrointestinal tract. *Proc Natl Acad Sci USA* 99: 14422-14427

Schwartz, R F, Neu J, Schatz D, Atkinson M A, Wasserfall C (2007) Comment on: Brugman S et al. (2006) Antibiotic treatment partially protects against type 1 diabetes in the Bio-Breeding diabetes-prone rat. Is the gut flora involved in the development of type 1 diabetes? *Diabetologia* 49: 2105-2108. *Diabetologia* 50: 220-221.

Silva M, Jacobus N V, Deneke C, Gorbach S L. (1987) Antimicrobial substance from a human *Lactobacillus* strain. Antimicrob. *Agents Chemother* 31: 1231-1213.

Stappenbeck T S, Hooper L V, Gordon J I. (2002) Developmental regulation of intestinal angiogenesis by indigenous microbes via Paneth cells. *Proc Natl Acad Sci USA* 99: 15451-15455.

Suzuki T, Yamada T, Fujimura T, Kawamura E, Shimizu M Yamashita R. (1987) Diabetogenic effects of lymphocyte transfusion on the NOD or NOD nude mouse. In "Immune-Deficient Animals in Biomedical Research, Copenhagen, 1985", Rygaard, Brunner N, Groem N, Spang-Thomsen M, eds, pp 112-116, Karger, Basel.

Tamura K, Dudley J, Nei M, Kumar S. (2007) MEGA4: Molecular Evolutionary Genetics Analysis (MEGA) software version 4.0. *Mol Biol Evol* 24: 1596-1599.

Taranto, M P, Medici M, Perdigon G, Ruiz Holgado A P, Valdez G F: Evidence for hypocholesterolemic effect of *Lactobacillus reuteri* in hypercholesterolemic mice. *J Dairy Sci* 81:2336-2340, 1998

Thompson J D, Gibson, T J, Plewniak F, Jeanmougin F, Higging D G. (1997) The CLUSTAL-X windows interface: flexible strategies for multiple sequence alignment aided by quality tools. *Nucleic Acids Res* 25: 4876-4882.

Vaarala O, Atkinson M A, Neu J (2008) The "Perfect Storm" for Type 1 Diabetes: The complex interplay between intestinal microbiota, gut permeability, and mucosal immunity. *Diabetes* (in press).

Yadav H, Shalini J, Sinha P R (2007) Antidiabetic effect of probiotic dahi containing *Lactobacillus acidophilus* and *Lactobacillus casei* in high fructose fed rats. *Nutrition* 23: 62-68.

Vandenbergh P A. (1993) Lactic acid bacteria, their metabolic products and interference with microbial growth. *FEMS Micorbiol Rev* 12: 221-238.

Wicker L S, Miller B J, Coker L Z, McNally S E, Scott S, Mullen Y, Appel M C (1987) Genetic control of diabetes and insulitis in the nonobese diabetic (NOD) mouse. *J Exp Med* 165:1639-1654.

The invention claimed is:

1. A method for improving immune function in a subject, wherein said method comprises administering to a subject in need of such improvement, an effective amount of an isolated probiotic bacteria strain, wherein the probiotic bacteria strain is *Lactobacillus johnsonii* N6.2 having ATCC Accession No. PTA-122064.

2. The method, according to claim 1, wherein the subject is a human.

3. The method, according to claim 1, wherein the method increases production of an anti-inflammatory agent, increases cyclooxygenase 2 (Cox-2) expression, decreases inducible nitric oxide synthase (iNOS) expression, decreases superoxide dismutase 2 (Sod2) expression, decreases expression of one or more pro-inflammatory cytokines, decreases expression of Indoleamine 2,3-Dioxygenase, decreases passage of one or more pro-inflammatory agents through gastrointestinal epithelia, increases the number of goblet cells, increases mucus production in the gastrointestinal tract, increases claudin 1 expression, inhibits enteric bacteria growth, and/or reduces translocation of enteric bacteria from the gastrointestinal tract.

4. The method, according to claim 3, wherein the pro-inflammatory cytokine is interferon (INF) gamma, Tumor necrosis factor (TNF), alpha, or both.

* * * * *

SEQUENCE LISTING

```
<160> NUMBER OF SEQ ID NOS: 71

<210> SEQ ID NO 1
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 1
gaggcagcag tagggaatct tc                                              22

<210> SEQ ID NO 2
<211> LENGTH: 27
<212> TYPE: DNA
<213> ORGANISM: Artificial Sequence
<220> FEATURE:
<223> OTHER INFORMATION: Sequence is synthesized

<400> SEQUENCE: 2
ggccagttac tacctctatc cttcttc                                         27

<210> SEQ ID NO 3
<211> LENGTH: 17
<212> TYPE: DNA
<213> ORGANISM: Artificial Sequence
<220> FEATURE:
<223> OTHER INFORMATION: Sequence is synthesized

<400> SEQUENCE: 3
cgcgtcyggt gtgaaag                                                    17

<210> SEQ ID NO 4
<211> LENGTH: 18
<212> TYPE: DNA
```

```
<213> ORGANISM: Artificial Sequence
<220> FEATURE:
<223> OTHER INFORMATION: Sequence is synthesized

<400> SEQUENCE: 4
ccccacatcc agcatcca                                                     18

<210> SEQ ID NO 5
<211> LENGTH: 38
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (33)..(33)
<223> OTHER INFORMATION: n is a, c, g, or t

<400> SEQUENCE: 5
gccttgccag cccgctcagt cattagatac ccnggtag                               38

<210> SEQ ID NO 6
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 6
gcctccctcg cgccatcaga agccgtttcg ntaccttgtt acgactt                     47

<210> SEQ ID NO 7
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 7
gcctccctcg cgccatcaga cacacactcg ntaccttgtt acgactt                     47

<210> SEQ ID NO 8
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 8
gcctccctcg cgccatcaga gacacagtcg ntaccttgtt acgactt                     47

<210> SEQ ID NO 9
<211> LENGTH: 47
<212> TYPE: DNA
<213> ORGANISM: Artificial Sequence
<220> FEATURE:
<223> OTHER INFORMATION: Sequence is synthesized
```

```
<220> FEATURE:
<221> NAME/KEY: misc_feature
<222> LOCATION: (31)..(31)
<223> OTHER INFORMATION: n is a, c, g, or t

<400> SEQUENCE: 9
gcctccctcg cgccatcaga taaccgctcg ntaccttgtt acgactt        47

<210> SEQ ID NO 10
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 10
gcctccctcg cgccatcagc aacaccatcg ntaccttgtt acgactt        47

<210> SEQ ID NO 11
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<220> FEATURE:
<221> NAME/KEY: misc_feature
<222> LOCATION: (31)..(31)
<223> OTHER INFORMATION: n is a, c, g, or t

<400> SEQUENCE: 11
gcctccctcg cgccatcagc caaccaatcg ntaccttgtt acgactt        47

<210> SEQ ID NO 12
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 12
gcctccctcg cgccatcagc gaaccattcg ntaccttgtt acgactt        47

<210> SEQ ID NO 13
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 13
gcctccctcg cgccatcagc tacaccttcg ntaccttgtt acgactt        47

<210> SEQ ID NO 14
<211> LENGTH: 47
```

```
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 14
gcctccctcg cgccatcagg aacaccttcg ntaccttgtt acgactt        47

<210> SEQ ID NO 15
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 15
gcctccctcg cgccatcagg caaccattcg ntaccttgtt acgactt        47

<210> SEQ ID NO 16
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 16
gcctccctcg cgccatcagg gaaccaatcg ntaccttgtt acgactt        47

<210> SEQ ID NO 17
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 17
gcctccctcg cgccatcagg tacaccatcg ntaccttgtt acgactt        47

<210> SEQ ID NO 18
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 18
gcctccctcg cgccatcagt aatccggtcg ntaccttgtt acgactt        47

<210> SEQ ID NO 19
```

```
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 19
gcctccctcg cgccatcagt cacacagtcg ntaccttgtt acgactt            47

<210> SEQ ID NO 20
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 20
gcctccctcg cgccatcagt gacacactcg ntaccttgtt acgactt            47

<210> SEQ ID NO 21
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 21
gcctccctcg cgccatcagt taaccggtcg ntaccttgtt acgactt            47

<210> SEQ ID NO 22
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 22
gcctccctcg cgccatcaga aggatcgtcg ntaccttgtt acgactt            47

<210> SEQ ID NO 23
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 23
gcctccctcg cgccatcaga ccatgcatcg ntaccttgtt acgactt            47
```

```
<210> SEQ ID NO 24
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 24
gcctccctcg cgccatcaga gacagtgtcg ntaccttgtt acgactt            47

<210> SEQ ID NO 25
<211> LENGTH: 47
<212> TYPE: DNA
<213> ORGANISM: Artificial Sequence
<220> FEATURE:
<223> OTHER INFORMATION: Sequence is synthesized
<220> FEATURE:
<221> NAME/KEY: misc_feature
<222> LOCATION: (31)..(31)
<223> OTHER INFORMATION: n is a, c, g, or t

<400> SEQUENCE: 25
gcctccctcg cgccatcagc aactgcatcg ntaccttgtt acgactt            47

<210> SEQ ID NO 26
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 26
cggtgaatac gttcccgg                                            18

<210> SEQ ID NO 27
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 27
tacggctacc ttgttacgac tt                                       22

<210> SEQ ID NO 28
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 28
gaggcagcag tagggaatct tc                                       22

<210> SEQ ID NO 29
<211> LENGTH: 27
<212> TYPE: DNA
<213> ORGANISM: Artificial Sequence
<220> FEATURE:
<223> OTHER INFORMATION: Sequence is synthesized

<400> SEQUENCE: 29
ggccagttac tacctctatc cttcttc                                  27
```

-continued

```
<210> SEQ ID NO 30
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 30
gagaggaagg tcccccac                                                18

<210> SEQ ID NO 31
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 31
cgctacttgg ctggttcag                                               19

<210> SEQ ID NO 32
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 32
gacgccgcgt gaagga                                                  16

<210> SEQ ID NO 33
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 33
agccccagcc tttcacatc                                               19

<210> SEQ ID NO 34
<211> LENGTH: 23
<212> TYPE: DNA
<213> ORGANISM: Artificial Sequence
<220> FEATURE:
<223> OTHER INFORMATION: Sequence is synthesized

<400> SEQUENCE: 34
tgccgtaact tcgggagaag gca                                          23

<210> SEQ ID NO 35
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 35
tcaaggacca gtgttcagtg tc                                           22

<210> SEQ ID NO 36
<211> LENGTH: 20
<212> TYPE: DNA
<213> ORGANISM: Artificial Sequence
<220> FEATURE:
<223> OTHER INFORMATION: Sequence is synthesized
```

<400> SEQUENCE: 36
atcagagggg gataacactt                                               20

<210> SEQ ID NO 37
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 37
actctcatcc ttgttcttct c                                             21

<210> SEQ ID NO 38
<211> LENGTH: 23
<212> TYPE: DNA
<213> ORGANISM: Artificial Sequence
<220> FEATURE:
<223> OTHER INFORMATION: Sequence is synthesized

<400> SEQUENCE: 38
caaaactact gagctagagt acg                                           23

<210> SEQ ID NO 39
<211> LENGTH: 25
<212> TYPE: DNA
<213> ORGANISM: Artificial Sequence
<220> FEATURE:
<223> OTHER INFORMATION: Sequence is synthesized

<400> SEQUENCE: 39
taagatctca aggatcccaa cggct                                         25

<210> SEQ ID NO 40
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 40
acggtcttgc tgtcacttat a                                             21

<210> SEQ ID NO 41
<211> LENGTH: 24
<212> TYPE: DNA
<213> ORGANISM: Artificial Sequence
<220> FEATURE:
<223> OTHER INFORMATION: Sequence is synthesized

<400> SEQUENCE: 41
tacacatatg ttcttcccta ataa                                          24

<210> SEQ ID NO 42
<211> LENGTH: 17
<212> TYPE: DNA
<213> ORGANISM: Artificial Sequence
<220> FEATURE:
<223> OTHER INFORMATION: Sequence is synthesized

<400> SEQUENCE: 42
cgcgtcyggt gtgaaag                                                  17

<210> SEQ ID NO 43

```
<211> LENGTH: 18
<212> TYPE: DNA
<213> ORGANISM: Artificial Sequence
<220> FEATURE:
<223> OTHER INFORMATION: Sequence is synthesized

<400> SEQUENCE: 43
ccccacatcc agcatcca                                                    18

<210> SEQ ID NO 44
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 44
tgacaggtgc agaaggaga                                                   19

<210> SEQ ID NO 45
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 45
tagagccacc aatccacaca                                                  20

<210> SEQ ID NO 46
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 46
aggtctggcg acattagtgg                                                  20

<210> SEQ ID NO 47
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 47
tggtgttggg taagaggttg                                                  20

<210> SEQ ID NO 48
<211> LENGTH: 23
<212> TYPE: DNA
<213> ORGANISM: Artificial Sequence
<220> FEATURE:
<223> OTHER INFORMATION: Sequence is synthesized

<400> SEQUENCE: 48
gctcagggaa tatccaccta tca                                              23

<210> SEQ ID NO 49
<211> LENGTH: 24
<212> TYPE: DNA
<213> ORGANISM: Artificial Sequence
<220> FEATURE:
<223> OTHER INFORMATION: Sequence is synthesized

<400> SEQUENCE: 49
```

```
cacaaagttt aacttccca gacg                                              24

<210> SEQ ID NO 50
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 50
ggactactac gccaaagaag                                                  20

<210> SEQ ID NO 51
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 51
tcaaaagaca gccactcagg                                                  20

<210> SEQ ID NO 52
<211> LENGTH: 23
<212> TYPE: DNA
<213> ORGANISM: Artificial Sequence
<220> FEATURE:
<223> OTHER INFORMATION: Sequence is synthesized

<400> SEQUENCE: 52
aggatgcatt catgagcatc gcc                                              23

<210> SEQ ID NO 53
<211> LENGTH: 23
<212> TYPE: DNA
<213> ORGANISM: Artificial Sequence
<220> FEATURE:
<223> OTHER INFORMATION: Sequence is synthesized

<400> SEQUENCE: 53
caccgactcc ttttccgctt cct                                              23

<210> SEQ ID NO 54
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 54
tcttctcatt cctgctcgtg                                                  20

<210> SEQ ID NO 55
<211> LENGTH: 19
<212> TYPE: DNA
<213> ORGANISM: Artificial Sequence
<220> FEATURE:
<223> OTHER INFORMATION: Sequence is synthesized

<400> SEQUENCE: 55
gatgagaggg agcccattt                                                   19

<210> SEQ ID NO 56
<211> LENGTH: 23
<212> TYPE: DNA
```

```
<213> ORGANISM: Artificial Sequence
<220> FEATURE:
<223> OTHER INFORMATION: Sequence is synthesized

<400> SEQUENCE: 56
ctcactgtgg ctgtggtcac cta                                              23

<210> SEQ ID NO 57
<211> LENGTH: 21
<212> TYPE: DNA
<213> ORGANISM: Artificial Sequence
<220> FEATURE:
<223> OTHER INFORMATION: Sequence is synthesized

<400> SEQUENCE: 57
gggtcttcgg gcttcaggtt a                                                21

<210> SEQ ID NO 58
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 58
cggtttcccg tgcaatcagt                                                  20

<210> SEQ ID NO 59
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 59
acaccgggga ccaaatgatg                                                  20

<210> SEQ ID NO 60
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 60
cgaccgaggg attccagatg                                                  20

<210> SEQ ID NO 61
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 61
atccgggtct tcctgtgcaa                                                  20

<210> SEQ ID NO 62
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 62
agcccacagc ggaagtcaac                                                  20
```

<210> SEQ ID NO 63
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 63
caatgtaacc ggcacccaca                                               20

<210> SEQ ID NO 64
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 64
gcggtgaacc agttgtggtg                                               20

<210> SEQ ID NO 65
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 65
agccacattg cccaggtctc                                               20

<210> SEQ ID NO 66
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 66
agctgcacca cagcaagcac                                               20

<210> SEQ ID NO 67
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 67
tccaccaccc ttagggctca                                               20

<210> SEQ ID NO 68
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 68
ctctgcgatg ctcttccgag                                               20

<210> SEQ ID NO 69
<211> LENGTH: 20
<212> TYPE: DNA
<213> ORGANISM: Artificial Sequence
<220> FEATURE:

```
<223> OTHER INFORMATION: Sequence is synthesized

<400> SEQUENCE: 69
aaggatttgc tgcatggctg                                              20

<210> SEQ ID NO 70
<211> LENGTH: 20
<212> TYPE: DNA
<213> ORGANISM: Artificial Sequence
<220> FEATURE:
<223> OTHER INFORMATION: Sequence is synthesized

<400> SEQUENCE: 70
gctgcctccc attctgtctt                                              20

<210> SEQ ID NO 71
<211> LENGTH: 22
<212> TYPE: DNA
<213> ORGANISM: Artificial Sequence
<220> FEATURE:
<223> OTHER INFORMATION: Sequence is synthesized

<400> SEQUENCE: 71
tgcgatttcc accattagag ag                                           22
```